United States Patent
Gaufreteau et al.

(10) Patent No.: US 10,457,667 B2
(45) Date of Patent: Oct. 29, 2019

(54) INDOLIN-2-ONE DERIVATIVES

(71) Applicant: Hoffmann-La Roche Inc., Little Falls, NJ (US)

(72) Inventors: Delphine Gaufreteau, Basel (CH); Hans Hilpert, Basel (CH); Roland Humm, Basel (CH); Sabine Kolczewski, Basel (CH); Thorsten Muser, Basel (CH); Jean-Marc Plancher, Basel (CH); Theodor Stoll, Basel (CH)

(73) Assignee: Hoffmann-La Roche Inc., Little Falls, NJ (US)

( * ) Notice: Subject to any disclaimer, the term of this patent is extended or adjusted under 35 U.S.C. 154(b) by 0 days.

(21) Appl. No.: 15/971,399

(22) Filed: May 4, 2018

(65) Prior Publication Data

US 2018/0251451 A1 Sep. 6, 2018

Related U.S. Application Data

(63) Continuation of application No. PCT/EP2016/076472, filed on Nov. 3, 2016.

(30) Foreign Application Priority Data

Nov. 6, 2015 (EP) .................................. 15193418

(51) Int. Cl.
  *C07D 403/14* (2006.01)
  *C07D 401/14* (2006.01)
  (Continued)

(52) U.S. Cl.
  CPC .......... *C07D 403/14* (2013.01); *A61P 25/08* (2018.01); *A61P 25/16* (2018.01); *A61P 25/18* (2018.01);
  (Continued)

(58) Field of Classification Search
  CPC .................................................. C07D 403/14
  (Continued)

(56) References Cited

U.S. PATENT DOCUMENTS 6,090,818 A 7/2000 Foulon et al.
9,616,053 B2 4/2017 Brunner et al.
(Continued)

FOREIGN PATENT DOCUMENTS

CA 2196809 7/1995
EP 2895476 6/2016
(Continued)

OTHER PUBLICATIONS (ISR and Written Opinion of PCT/EP2015/064016 (dated Aug. 4, 2015)).
(Continued)

*Primary Examiner* — Kahsay Habte
(74) *Attorney, Agent, or Firm* — Todd M. Crissey

(57) ABSTRACT

The present invention is concerned with indolin-2-one derivatives of general formula

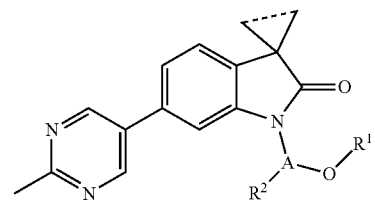

wherein
A is phenyl or a six membered heteroaryl group, containing one or two N atoms, selected from

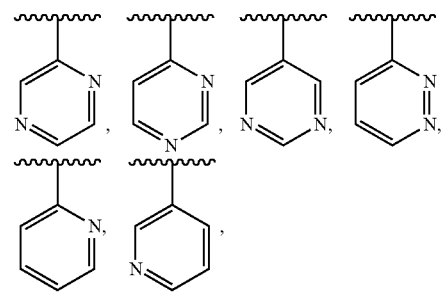

or the oxygen atom may form together with two neighboring carbon atoms from the group A an additional fused ring, selected from

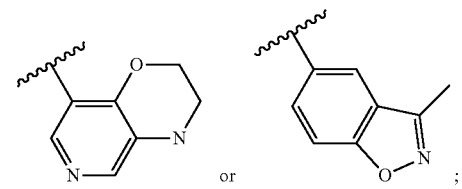

$R^1$ is hydrogen, lower alkyl, lower alkyl substituted by halogen or oxetanyl;
$R^2$ is hydrogen, lower alkyl lower alkoxy, halogen or cycloalkyl;
--- the dotted line is nothing or may be —$CH_2$—;
as well as with a pharmaceutically acceptable salt thereof, with a racemic mixture, or with its corresponding enantiomer and/or optical isomer and/or stereoisomer thereof.

(Continued)

The compounds may be used in the treatment of CNS diseases related to positive (psychosis) and negative symptoms of schizophrenia, substance abuse, alcohol and drug addiction, obsessive-compulsive disorders, cognitive impairment, bipolar disorders, mood disorders, major depression, treatment resistant depression, anxiety disorders, Alzheimer's disease, autism, Parkinson's disease, chronic pain, borderline personality disorder, neurodegenerative disease, sleep disturbances, chronic fatigue syndrome, stiffness, inflammatory disease, asthma, Huntington's disease, ADHD, amyotrophic lateral sclerosis, effects in arthritis, autoimmune disease, viral and fungal infections, cardiovascular diseases, ophthalmology and inflammatory retinal diseases and balance problems, epilepsy and neurodevelopmental disorders with co morbid epilepsy.

26 Claims, No Drawings

(51) Int. Cl.
| | |
|---|---|
| C07D 403/10 | (2006.01) |
| C07D 498/04 | (2006.01) |
| A61P 25/36 | (2006.01) |
| A61P 25/28 | (2006.01) |
| A61P 25/22 | (2006.01) |
| A61P 25/32 | (2006.01) |
| A61P 25/18 | (2006.01) |
| A61P 25/24 | (2006.01) |
| A61P 25/08 | (2006.01) |
| A61P 25/16 | (2006.01) |
| C07D 403/04 | (2006.01) |
| C07D 405/14 | (2006.01) |
| C07D 413/14 | (2006.01) |
| A61K 31/506 | (2006.01) |
| A61K 45/06 | (2006.01) |

(52) U.S. Cl.
CPC .............. *A61P 25/22* (2018.01); *A61P 25/24* (2018.01); *A61P 25/28* (2018.01); *A61P 25/32* (2018.01); *A61P 25/36* (2018.01); *C07D 401/14* (2013.01); *C07D 403/04* (2013.01); *C07D 403/10* (2013.01); *C07D 405/14* (2013.01); *C07D 413/14* (2013.01); *C07D 498/04* (2013.01); *A61K 31/506* (2013.01); *A61K 45/06* (2013.01); *A61K 2300/00* (2013.01)

(58) Field of Classification Search
USPC ........................................................ 514/256
See application file for complete search history.

(56) References Cited

U.S. PATENT DOCUMENTS

| | | |
|---|---|---|
| 2006/0253263 A1 | 11/2006 | Meshkin |
| 2008/0039496 A1 | 2/2008 | Blackburn et al. |
| 2011/0053936 A1 | 3/2011 | Eastwood et al. |
| 2016/0095844 A1 | 4/2016 | Brunner et al. |
| 2017/0101409 A1 | 4/2017 | Hilpert et al. |
| 2018/0251449 A1 | 9/2018 | Gaufreteau et al. |
| 2018/0251450 A1 | 9/2018 | Gaufreteau et al. |
| 2018/0251451 A1 | 9/2018 | Gaufreteau et al. |
| 2018/0251455 A1 | 9/2018 | Gaufreteau et al. |

FOREIGN PATENT DOCUMENTS

| | | |
|---|---|---|
| JP | 10-503503 | 3/1998 |
| JP | H10-503503 A | 3/1998 |
| JP | 2004-501192 A | 1/2004 |
| JP | 2008-536941 A | 9/2008 |
| JP | 2009-541493 | 11/2009 |
| JP | 2009-541493 A | 11/2009 |
| TW | 201504223 A | 2/2015 |
| WO | 91/06545 A1 | 5/1991 |
| WO | 94/10171 | 5/1994 |
| WO | 96/04272 | 2/1996 |
| WO | 98/25901 A1 | 6/1998 |
| WO | 00/40581 | 7/2000 |
| WO | 02/00217 A1 | 1/2002 |
| WO | 2004/060902 A2 | 7/2004 |
| WO | 2005/108388 A1 | 11/2005 |
| WO | 2006/113864 A2 | 10/2006 |
| WO | 2006/113875 A2 | 10/2006 |
| WO | 2008/002946 A2 | 1/2008 |
| WO | 2008/046083 A2 | 4/2008 |
| WO | 2008/080970 A1 | 7/2008 |
| WO | 2008/080973 | 7/2008 |
| WO | 2009/124692 A1 | 10/2009 |
| WO | 2009/132774 A1 | 11/2009 |
| WO | 2010/066684 A2 | 6/2010 |
| WO | 2014/040969 A1 | 3/2014 |
| WO | 2014/202493 A1 | 12/2014 |
| WO | 2015/197567 | 12/2015 |
| WO | 2017/076842 | 5/2017 |
| WO | 2017/076852 | 5/2017 |
| WO | 2017/076931 | 5/2017 |
| WO | 2017/076932 | 5/2017 |

OTHER PUBLICATIONS

Anne E. King et al., "Nucleoside transporters: from scavengers to novel therapeutic targets" Trends in Pharmacological Science 27(8):416-425 ( 2006).

Daniela Alberati et al., "Pharmacological evaluation of a novel assay for detecting glycine transporter 1 inhibitors and their antipsychotic potential" Pharmacology, Biochemistry and Behavior 97:185-191 ( 2010).

Elena P. Calandre et al., "The Role of Antipsychotics in the Management of Fibromyalgia" CNS Drugs 26(2):135-153 ( 2012).

Gregory I Liou et al., "Diabetic retinopathy: Role of inflammation and potential therapies for anti-inflammation" World Journal of Diabetes 1(1):12-18 (Mar. 15, 2010).

ISR and Written Opinion of PCT/EP2016/076332 (dated Dec. 8, 2016).

ISR and Written Opinion of PCT/EP2016/076472 (dated Dec. 12, 2016).

ISR of PCT/EP2016/076315 (dated Jan. 4, 2017).

ISR of PCT/EP2016/076473 (dated Dec. 21, 2016).

INDOLIN-2-ONE DERIVATIVES

RELATED APPLICATIONS

This application is a continuation of International Application No. PCT/EP2016/076472, filed Nov. 3, 2016, claiming priority to application Ser. No. 15/193,418.9, filed Nov. 6, 2015, each of which are incorporated herein by reference in its entirety.

The present invention is concerned with indolin-2-one derivatives of general formula

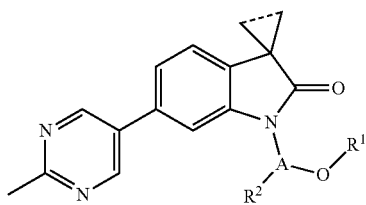

wherein

A is phenyl or a six membered heteroaryl group, containing one or two N atoms, selected from

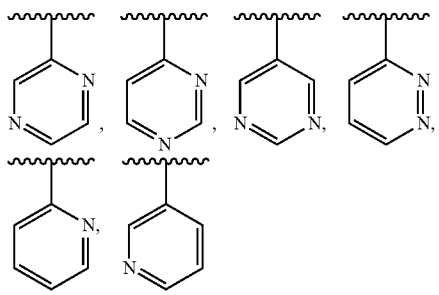

or the oxygen atom may form together with two neighboring carbon atoms from the group A an additional fused ring, selected from

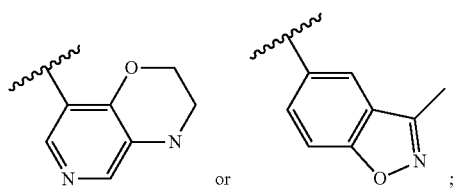 [SMILES: *c1cncc2c1OCCN2 ; *c1ccc2onc(C)c2c1]

$R^1$ is hydrogen, lower alkyl, lower alkyl substituted by halogen or oxetanyl;
$R^2$ is hydrogen, lower alkyl lower alkoxy, halogen or cycloalkyl;
--- the dotted line is nothing or may be —$CH_2$—;
as well as with a pharmaceutically acceptable salt thereof, with a racemic mixture, or with its corresponding enantiomer and/or optical isomer and/or stereoisomer thereof.

The $OR^1$ group and $R^2$ may have different positions on A.

Now it has been found that the compounds of formula I may be used for the treatment of CNS diseases. The described compounds have been shown to reverse the L-687,414 ((3R,4R)-3 amino-1-hydroxy-4-methyl-pyrrolidin-2-one, a NMDA glycine site antagonist) induced hyperlocomotion, a behavioral pharmacodynamic mouse model for schizophrenia, described by D. Alberati et al. in *Pharmacology, Biochemistry and Behavior*, 97 (2010), 185-191. The Pop/Feb. 8, 2016
authors described that hyperlocomotion induced by L-687,414 was inhibited by a series of known antipsychotic drugs. The compounds of formula I demonstrate marked activity in this model. These findings predict antipsychotic activity for the present compounds, making them useful for the treatment of positive (psychosis) and negative symptoms of schizophrenia, substance abuse, alcohol and drug addiction, obsessive-compulsive disorders, cognitive impairment, bipolar disorders, mood disorders, major depression, resistant depression, anxiety disorders, Alzheimer's disease, autism, Parkinson's disease, chronic pain, borderline personality disorder, sleep disturbances, chronic fatigue syndrome, stiffness, antiinflammatory effects in arthritis and balance problems, epilepsy and neurodevelopmental disorders with co morbid epilepsy.

In addition to the reversal of L-687,414 induced hyperlocomotion experiment as described above, some compounds of the present invention have been tested in SmartCube®, an automated system in which the behaviors of compound-treated mice in response to multiple challenges are captured by digital video and analyzed with computer algorithms (Roberds et al., *Frontiers in Neuroscience*, 2011, Vol. 5, Art. 103, 1-4; Vadim Alexandrov, Dani Brunner, Taleen Hanania, Emer Leahy *Eur. J. Pharmacol.* 2015, 750, 82-99). In this way, the neuro-pharmacological effects of a test compound can be predicted by similarity to major classes of compounds, such as antipsychotics, anxiolytics and antidepressants. Examples 2 and 12 show similarity to atypical antipsychotics. The results are shown in Table 3.

In addition to the above-mentioned experiments, it has been shown that some of the compounds of formula I are also ENT1 inhibitors (equilibrative nucleoside transporter 1 protein). Therapeutic potential of ENT1 inhibitors is directly or indirectly (via effects of adenosine and/or adenosine receptor modulation) described in the literature for the treatment of the following diseases:
autoimmune disease (US 2006/253263), cancer (WO9857643), viral infections and fungal infections (WO2004060902), neurodegenerative disease, Parkinson's disease, Alzheimer's disease, Huntington's disease, amyotrophic lateral sclerosis, psychiatric diseases, substance abuse, ADHD, depression, epilepsy, anxiety, schizophrenia (WO0168105, EP 1252910, EP1612210, WO2009018275), autism spectrum disorders (Susan A. Masinoa, Masahito Kawamura Jr., Jessica L. Cotea, Rebecca B. Williams, David N. Ruskina, *Neuropharmacology*, 2013, 68, 116-121, pain (WO2009062990, WO2009064497), inflammation, asthma, (US 2007213296, *Inflammation research*, 2011, 60, 75-76), cardiovascular diseases (*Trends in Pharmacological science*, 2006, 27, 416-425), sleep disorders, (*Psychopharmacology*, 1987, 91, 434-439), ophthalmology and inflammatory retinal diseases (*World Journal of Diabetes*, vol. 1, 12-18), epilepsy and neurodevelopmental disorders with co morbid epilepsy (*ENT1 Inhibition Attenuates Epileptic Seizure Severity Via Regulation of Glutamatergic Neurotransmission*, Xu et al, *Neuromol Med* (2015) 17:1-11, *Epigenetic changes induced by adenosine augmentation therapy prevent epileptogenesis*, Williams-Karnesky et al, *J Clin Invest.* 2013 August; 123(8):3552-63).

Schizophrenia is a complex mental disorder typically appearing in late adolescence or early adulthood with a world-wide prevalence of approximately 1% of the adult population, which has enormous social and economic impact. The criteria of the Association of European Psychiatrists (ICD) and the American Psychiatric Association (DSM) for the diagnosis of schizophrenia require two or more characteristic symptoms to be present: delusions, hallucinations, disorganized speech, grossly disorganized or catatonic behavior (positive symptoms), or negative symptoms (alogia, affective flattening, lack of motivation, anhedonia). As a group, people with schizophrenia have functional impairments that may begin in childhood, continue throughout adult life and make most patients unable to maintain normal employment or otherwise have normal social function. They also have a shortened lifespan compared to the general population, and suffer from an increased prevalence of a wide variety of other neuropsychiatric syndromes, including substance abuse, obsessive-compulsive symptoms and abnormal involuntary movements. Schizophrenia is also associated with a wide range of cognitive impairments, bipolar disorders, major depression and anxiety disorders, the severity of which limits the functioning of patients, even when psychotic symptoms are well controlled. The primary treatment of schizophrenia is antipsychotic medications. Antipsychotics, for example risperidone and olanzapine, however, fail to significantly ameliorate the negative symptoms and cognitive dysfunction.

Antipsychotic drugs have shown clinical efficacy for the treatment of the following diseases:

Fibromyalgia, which is a syndrome characterized by chronic generalized pain associated with different somatic symptoms, such as sleep disturbances, fatigue, stiffness, balance problems, hypersensitivity to physical and psychological environmental stimuli, depression and anxiety (*CNS Drugs*, 2012, 26, 2, 135-53).

Schizoaffective disorders: includes psychotic and affective symptoms, this disorder falls on a spectrum between bipolar disorders (with depressive and manic episodes, alcohol and drug addiction, substance abuse) and schizophrenia. *J. Clin. Psychiatry*, 2010, 71, S2, 14-9, *Pediatr. Drugs* 2011, 13, 5, 291-302

Major depression: *BMC Psychiatry* 2011, 11, 86

Treatment resistant depression: *Journal of Psychopharmacology*, 0(0) 1-16

Anxiety: *European Neuropsychopharmacology*, 2011, 21, 429-449

Bipolar disorders: *Encephale, International J. of Neuropsychopharmacology*, 2011, 14, 1029-104, *International J. of Neuropsychopharmacology*, 2012, 1-12; *J of Neuropsychopharmacology*, 2011, 0, 0, 1-15

Mood disorders: *J Psychopharmacol.* 2012, January 11, *CNS Drugs*, 2010, 2, 131-61

Autism: *Current opinion in pediatrics*, 2011, 23, 621-627; *J. Clin. Psychiatry*, 2011, 72, 9, 1270-1276

Alzheimer's disease: *J Clin. Psychiatry*, 2012, 73, 1, 121-128

Parkinson's disease: *Movement Disorders*, 2011, 26, 6

Chronic fatigue syndrome: *European Neuropsychopharmacology*, 2011, 21, 282-286

Borderline Personality disorder: *J Clin. Psychiatry*, 2011, 72, 10, 1363-1365 *J. Clin. Psychiatry*, 2011, 72, 10, 1353-1362

Anti-inflammatory effects in arthritis: *European J. of Pharmacology*, 2012, 678, 55-60

Objects of the present invention are novel compounds of formula I and the use of compounds of formula I and their pharmaceutically acceptable salts for the treatment of CNS diseases related to positive (psychosis) and negative symptoms of schizophrenia, substance abuse, alcohol and drug addiction, obsessive-compulsive disorders, cognitive impairment, bipolar disorders, mood disorders, major depression, treatment resistant depression, anxiety disorders, Alzheimer's disease, autism, Parkinson's disease, chronic pain, borderline personality disorder, neurodegenerative disease, sleep disturbances, chronic fatigue syndrome, stiffness, inflammatory disease, asthma, Huntington's disease, ADHD, amyotrophic lateral sclerosis, epilepsy, arthritis, autoimmune disease, viral and fungal infections, cardiovascular diseases, ophthalmology and inflammatory retinal diseases and balance problems, epilepsy and neurodevelopmental disorders with co morbid epilepsy.

Further objects of the present invention are medicaments containing such novel compounds as well as methods for preparation of compounds of formula I, a combination of compounds of formula I with marketed antipsychotics, antidepressants, anxiolytics or mood stabilizers, and methods for the treatment of CNS disorders as mentioned above.

Encompassed by the present invention are corresponding prodrugs of compounds of formula I.

A common antipsychotic drug for the treatment of schizophrenia is olanzapine. Olanzapine (Zyprexa) belongs to a drug class known as atypical antipsychotics. Other members of this class include for example clozapine (Clozaril), risperidone (Risperdal), aripiprazole (Abilify) and ziprasidone (Geodon).

Olanzapine is approved for the treatment of psychotic disorders, long term treatment of bipolar disorders and in combination with fluoxetine for the treatment of depressive episodes associated with bipolar disorders and for the treatment of resistant depression. The compounds of the present invention may be combined with antipsychotic drugs like olanzapine (Zyprexa), clozapine (Clozaril), risperidone (Risperdal), aripiprazole (Abilify), amisulpride (Solian), asenapine (Saphris), blonanserin (Lonasen), clotiapine (Entumine), iloperidone (Fanapt), lurasidone (Latuda), mosapramine (Cremin), paliperidone (Invega), perospirone (Lullan), quetiapine (Seroquel), remoxipride (Roxiam), sertindole (Serdolect), sulpiride (Sulpirid, Eglonyl), ziprasidone (Geodon, Zeldox), zotepine (Nipolept), haloperidol (Haldol, Serenace), droperidol (Droleptan), chlorpromazine (Thorazine, Largactil), fluphenazine (Prolixin), perphenazine (Trilafon), prochlorperazine (Compazine), thioridazine (Mellaril, Melleril), trifluoperazine (Stelazine), triflupromazine (Vesprin), levomepromazine (Nozinan), promethazine (Phenergan), pimozide (Orap) and cyamemazine (Tercian).

One preferred embodiment of the invention is a combination, wherein the marketed antipsychotic drug is olanzapine (Zyprexa), clozapine (Clozaril), risperidone (Risperdal), aripiprazole (Abilify) or ziprasidone.

Furthermore, the compounds of the present invention can be combined with antidepressants such as selective serotonin reuptake inhibitors [Citalopram (Celexa), Escitalopram (Lexapro, Cipralex), Paroxetine (Paxil, Seroxat), Fluoxetine (Prozac), Fluvoxamine (Luvox), Sertraline (Zoloft, Lustral)], serotonin-norepinephrine reuptake inhibitors [Duloxetine (Cymbalta), Milnacipran (Ixel, Savella), Venlafaxine (Effexor), Desvenlafaxine (Pristiq), Tramadol (Tramal, Ultram), Sibutramine (Meridia, Reductil)], serotonin antagonist and reuptake inhibitors [Etoperidone (Axiomin, Etonin), Lubazodone (YM-992, YM-35,995), Nefazodone (Serzone, Nefadar), Trazodone (Desyrel)], norepinephrine reuptake inhibitors [Reboxetine (Edronax), Viloxazine (Vivalan), Atomoxetine (Strattera)], norepinephrine-dopamine reuptake inhibitors [Bupropion (Wellbutrin, Zyban), Dexmethylphenidate (Focalin), Methylphenidate (Ritalin, Concerta)], norepinephrine-dopamine releasing agents [Amphetamine (Adderall), Dextroamphetamine (Dexedrine), Dextromethamphetamine (Desoxyn), Lisdexamfetamine (Vyvanse)], tricyclic antidepressants [Amitriptyline (Elavil, Endep), Clomipramine (Anafranil), Desipramine (Norpramin, Pertofrane), Dosulepin [Dothiepin] (Prothiaden), Doxepin (Adapin, Sinequan), Imipramine (Tofranil), Lofepramine (Feprapax, Gamanil, Lomont), Nortriptyline (Pamelor), Protriptyline (Vivactil), Trimipramine (Surmontil)], tetracyclic antidepressants [Amoxapine (Asendin), Maprotiline (Ludiomil), Mianserin (Bolvidon, Norval, Tolvon), Mirtazapine (Remeron)], monoamine oxidase inhibitors [Isocarboxazid (Marplan), Moclobemide (Aurorix, Manerix), Phenelzine (Nardil), Selegiline [L-Deprenyl] (Eldepryl, Zelapar, Emsam), Tranylcypromine (Parnate), Pirlindole (Pirazidol)], 5-HT1A Receptor Agonists [Buspirone (Buspar), Tandospirone (Sediel), Vilazodone (Viibryd)], 5-HT2 Receptor Antagonists [Agomelatine (Valdoxan), Nefazodone (Nefadar, Serzone), selective Serotonin Reuptake Enhancers [Tianeptine].

A preferred embodiment of this invention is a combination, wherein the marketed anti-depressive drug is citalopram (Celexa), escitalopram (Lexapro, Cipralex), paroxetine (Paxil, Seroxat), fluoxetine (Prozac), sertraline (Zoloft, Lustral) duloxetine (Cymbalta), milnacipran (Ixel, Savella), venlafaxine (Effexor), or mirtazapine (Remeron).

Compounds can also be combined with anxiolytics such as Alprazolam (Helex, Xanax, Xanor, Onax, Alprox, Restyl, Tafil, Paxal), Bretazenil, Bromazepam (Lectopam, Lexotanil, Lexotan, Bromam), Brotizolam (Lendormin, Dormex, Sintonal, Noctilan), Chlordiazepoxide (Librium, Risolid, Elenium), Cinolazepam (Gerodorm), Clonazepam (Rivotril, Klonopin, Iktorivil, Paxam), Clorazepate (Tranxene, Tranxilium), Clotiazepam (Veratran, Clozan, Rize), Cloxazolam (Sepazon, Olcadil), Delorazepam (Dadumir), Diazepam (Antenex, Apaurin, Apzepam, Apozepam, Hexalid, Pax, Stesolid, Stedon, Valium, Vival, Valaxona), Estazolam (ProSom), Etizolam (Etilaam, Pasaden, Depas), Flunitrazepam (Rohypnol, Fluscand, Flunipam, Ronal, Rohydorm), Flurazepam (Dalmadorm, Dalmane), Flutoprazepam (Restas), Halazepam (Paxipam), Ketazolam (Anxon), Loprazolam (Dormonoct), Lorazepam (Ativan, Temesta, Tavor, Lorabenz), Lormetazepam (Loramet, Noctamid, Pronoctan), Medazepam (Nobrium), Midazolam (Dormicum, Versed, Hypnovel, Dormonid), Nimetazepam (Erimin), Nitrazepam (Mogadon, Alodorm, Pacisyn, Dumolid, Nitrazadon), Nordazepam (Madar, Stilny), Oxazepam (Seresta, Serax, Serenid, Serepax, Sobril, Oxabenz, Oxapax), Phenazepam (Phenazepam), Pinazepam (Domar), Prazepam (Lysanxia, Centrax), Premazepam, Quazepam (Doral), Temazepam (Restoril, Normison, Euhypnos, Temaze, Tenox), Tetrazepam (Mylostan), Triazolam (Halcion, Rilamir), Clobazam (Frisium, Urbanol), Eszopiclone (Lunesta), Zaleplon (Sonata, Starnoc), Zolpidem (Ambien, Nytamel, Stilnoct, Stilnox, Zoldem, Zolnod), Zopiclone (Imovane, Rhovane, Ximovan; Zileze; Zimoclone; Zimovane; Zopitan; Zorclone), Pregabalin (Lyrica) and Gabapentin (Fanatrex, Gabarone, Gralise, Neurontin, Nupentin).

One preferred embodiment of the invention is a combination, wherein the marketed anxiolytic drug is alprazolam (Helex, Xanax, Xanor, Onax, Alprox, Restyl, Tafil, Paxal), chlordiazepoxide (Librium, Risolid, Elenium), clonazepam (Rivotril, Klonopin, Iktorivil, Paxam), diazepam (Antenex, Apaurin, Apzepam, Apozepam, Hexalid, Pax, Stesolid, Stedon, Valium, Vival, Valaxona), Estazolam (ProSom), eszopiclone (Lunesta), zaleplon (Sonata, Starnoc), zolpidem (Ambien, Nytamel, Stilnoct, Stilnox, Zoldem, Zolnod), pregabalin (Lyrica) or gabapentin (Fanatrex, Gabarone, Gralise, Neurontin, Nupentin).

A further object of the invention is a combination with mood stabilizers such as Carbamazepine (Tegretol), Lamotrigine (Lamictal), Lithium (Eskalith, Lithane, Lithobid), and Valproic Acid (Depakote).

Compounds can also be combined with procognitive compounds such as donepezil (Aricept), galantamine (Razadyne), rivastigmine (Exelon) and memantine (Namenda).

The preferred indications using the compounds of the present invention are psychotic diseases like schizophrenia.

As used herein, the term "lower alkyl" denotes a saturated straight- or branched-chain group containing from 1 to 7 carbon atoms, for example, methyl, ethyl, propyl, isopropyl, n-butyl, i-butyl, 2-butyl, t-butyl and the like. Preferred alkyl groups are groups with 1-4 carbon atoms.

As used herein, the term "lower alkoxy" denotes an alkyl group as defined above, wherein the alkyl residue is attached via an oxygen atom.

As used herein, the term "lower alkyl substituted by halogen" denotes a group wherein the alkyl residue is as defined above, wherein at least one hydrogen atom is replaced by a halogen atom.

The term "cycloalkyl" denotes an alkyl ring with 3-6 carbon ring atoms.

The term "halogen" denotes chlorine, iodine, fluorine and bromine.

The term "pharmaceutically acceptable acid addition salts" embraces salts with inorganic and organic acids, such as hydrochloric acid, nitric acid, sulfuric acid, phosphoric acid, citric acid, formic acid, fumaric acid, maleic acid, acetic acid, succinic acid, tartaric acid, methane-sulfonic acid, p-toluenesulfonic acid and the like.

One embodiment of the invention are compounds of formula IA

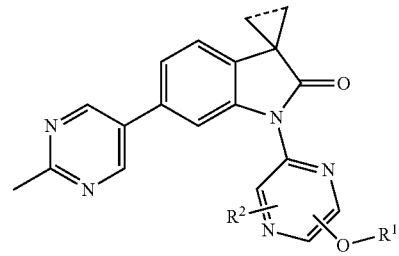

IA wherein
R¹ is hydrogen, lower alkyl, lower alkyl substituted by halogen or oxetanyl;
R² is hydrogen, lower alkyl lower alkoxy, halogen or cycloalkyl;
--- the dotted line is nothing or may be —CH₂—;
as well as a pharmaceutically acceptable salt thereof, a racemic mixture, or its corresponding enantiomer and/or optical isomer and/or stereoisomer thereof, for example the following compounds
1-(6-methoxypyrazin-2-yl)-3,3-dimethyl-6-(2-methylpyrimidin-5-yl)indolin-2-one or
1-(5-methoxypyrazin-2-yl)-3,3-dimethyl-6-(2-methylpyrimidin-5-yl)indolin-2-one.

One embodiment of the invention are compounds of formula IB

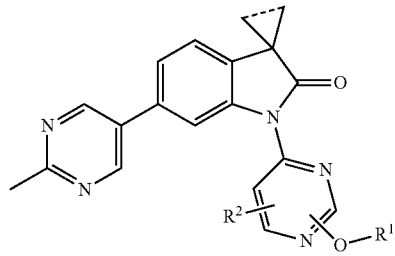

IB wherein

R¹ is hydrogen, lower alkyl, lower alkyl substituted by halogen or oxetanyl;

R² is hydrogen, lower alkyl lower alkoxy, halogen or cycloalkyl;

--- the dotted line is nothing or may be —CH₂—;

as well as a pharmaceutically acceptable salt thereof, a racemic mixture, or its corresponding enantiomer and/or optical isomer and/or stereoisomer thereof, for example the following compound 1-(2,6-dimethoxypyrimidin-4-yl)-3,3-dimethyl-6-(2-methylpyrimidin-5-yl)indolin-2-one.

One embodiment of the invention are compounds of formula IC

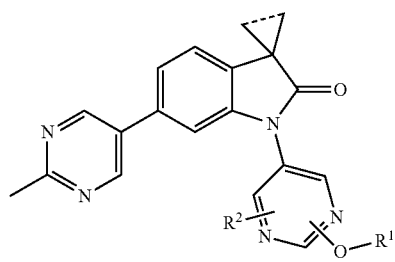

IC wherein

R¹ is hydrogen, lower alkyl, lower alkyl substituted by halogen or oxetanyl;

R² is hydrogen, lower alkyl lower alkoxy, halogen or cycloalkyl;

--- the dotted line is nothing or may be —CH₂—;

as well as a pharmaceutically acceptable salt thereof, a racemic mixture, or its corresponding enantiomer and/or optical isomer and/or stereoisomer thereof, for example the following compounds 1-(2-methoxypyrimidin-5-yl)-3,3-dimethyl-6-(2-methylpyrimidin-5-yl)indolin-2-one or 3,3-dimethyl-6-(2-methylpyrimidin-5-yl)-1-(2-(oxetan-3-yloxy)pyrimidin-5-yl)indolin-2-one.

One embodiment of the invention are compounds of formula ID

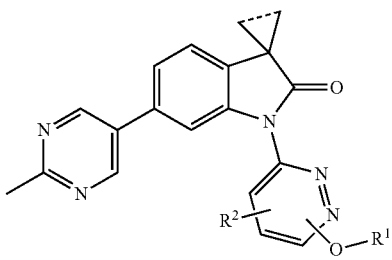

ID wherein

R¹ is hydrogen, lower alkyl, lower alkyl substituted by halogen or oxetanyl;

R² is hydrogen, lower alkyl lower alkoxy, halogen or cycloalkyl;

--- the dotted line is nothing or may be —CH₂—;

as well as a pharmaceutically acceptable salt thereof, a racemic mixture, or its corresponding enantiomer and/or optical isomer and/or stereoisomer thereof, for example the following compounds 1-(6-methoxypyridazin-3-yl)-3,3-dimethyl-6-(2-methylpyrimidin-5-yl)indolin-2-one 1-(6-hydroxypyridazin-3-yl)-3,3-dimethyl-6-(2-methylpyrimidin-5-yl)indolin-2-one or 1'-(6-methoxypyridazin-3-yl)-6'-(2-methylpyrimidin-5-yl)spiro[cyclobutane-1,3'-indolin]-2'-one.

One embodiment of the invention are compounds of formula IE

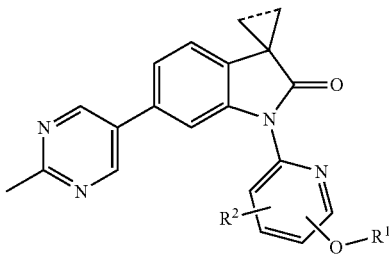

IE wherein

R¹ is hydrogen, lower alkyl, lower alkyl substituted by halogen or oxetanyl;

R² is hydrogen, lower alkyl lower alkoxy, halogen or cycloalkyl;

--- the dotted line is nothing or may be —CH₂—;

as well as a pharmaceutically acceptable salt thereof, a racemic mixture, or its corresponding enantiomer and/or optical isomer and/or stereoisomer thereof, for example the following compound 3,3-dimethyl-6-(2-methylpyrimidin-5-yl)-1-(5-(trifluoromethoxy)pyridin-2-yl)indolin-2-one.

One embodiment of the invention are compounds of formula IF

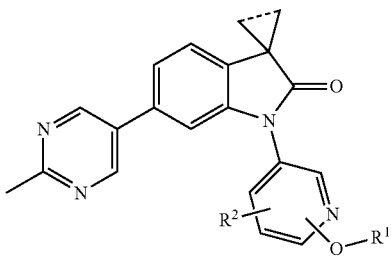

IF wherein
R¹ is hydrogen, lower alkyl, lower alkyl substituted by halogen or oxetanyl;
R² is hydrogen, lower alkyl lower alkoxy, halogen or cycloalkyl;
--- the dotted line is nothing or may be —CH₂—;
as well as a pharmaceutically acceptable salt thereof, a racemic mixture, or its corresponding enantiomer and/or optical isomer and/or stereoisomer thereof, for example the following compounds
1-(5-methoxypyridin-3-yl)-3,3-dimethyl-6-(2-methylpyrimidin-5-yl)indolin-2-one
1-(5-methoxy-6-methylpyridin-3-yl)-3,3-dimethyl-6-(2-methylpyrimidin-5-yl)indolin-2-one
1-(5-ethoxypyridin-3-yl)-3,3-dimethyl-6-(2-methylpyrimidin-5-yl)indolin-2-one
1-(5-isopropoxypyridin-3-yl)-3,3-dimethyl-6-(2-methylpyrimidin-5-yl)indolin-2-one
1-(6-chloro-5-methoxypyridin-3-yl)-3,3-dimethyl-6-(2-methylpyrimidin-5-yl)indolin-2-one
1-(6-cyclopropyl-5-methoxypyridin-3-yl)-3,3-dimethyl-6-(2-methylpyrimidin-5-yl)indolin-2-one
3,3-dimethyl-6-(2-methylpyrimidin-5-yl)-1-(6-(2,2,2-trifluoroethoxy)pyri din-3-yl)indolin-2-one or
1'-(5-methoxypyridin-3-yl)-6'-(2-methylpyrimidin-5-yl)spiro[cyclobutane-1,3'-indolin]-2'-one.

One embodiment of the invention are compounds of formula IG

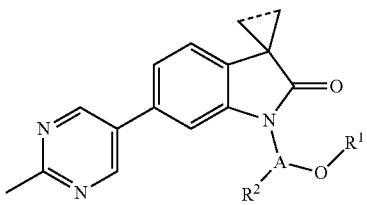

IG wherein
A is phenyl or

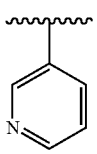

and the oxygen atom may form together with two neighboring carbon atoms from the group A an additional fused ring, selected from

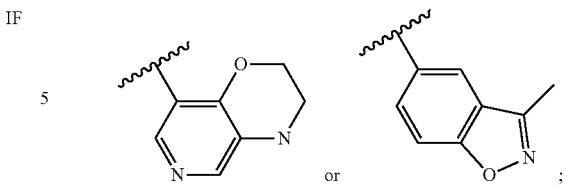

R¹ is hydrogen;
R² is hydrogen;
--- the dotted line is nothing or may be —CH₂—;
as well as a pharmaceutically acceptable salt thereof, a racemic mixture, or its corresponding enantiomer and/or optical isomer and/or stereoisomer thereof, for example the following compounds
1-(3,4-dihydro-2H-pyrido[3,2-b][1,4]oxazin-7-yl)-3,3-dimethyl-6-(2-methylpyrimidin-5-yl)indolin-2-one or
3,3-dimethyl-1-(3-methylbenzo[d]isoxazol-5-yl)-6-(2-methylpyrimidin-5-yl)indolin-2-one.

One embodiment of the invention are compounds of formula IH

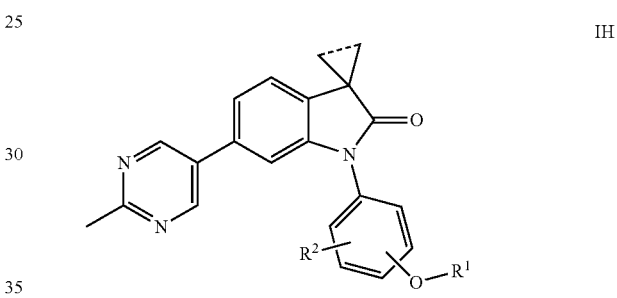

IH wherein
R¹ is hydrogen, lower alkyl, lower alkyl substituted by halogen or oxetanyl;
R² is hydrogen, lower alkyl lower alkoxy, halogen or cycloalkyl;
--- the dotted line is nothing or may be —CH₂—;
as well as a pharmaceutically acceptable salt thereof, a racemic mixture, or its corresponding enantiomer and/or optical isomer and/or stereoisomer thereof, for example the following compound
1-(3-methoxyphenyl)-3,3-dimethyl-6-(2-methylpyrimidin-5-yl)indolin-2-one.

The present compounds of formula I and their pharmaceutically acceptable salts can be prepared by methods known in the art, for example, by processes described below, which processes comprise
a) reacting a compound of formula

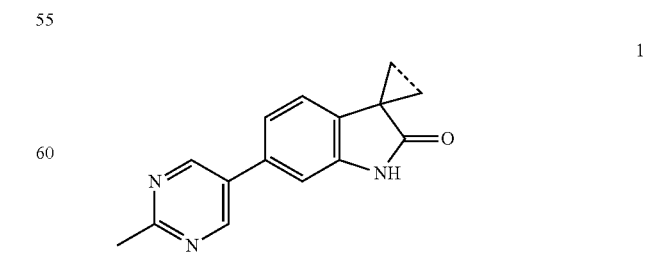

1 with a compound of formula

Y-A(R²)—O—R¹    2 to a compound of formula

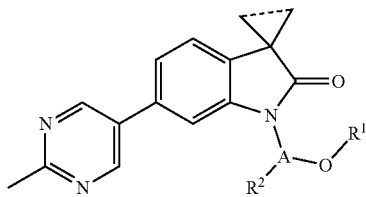

wherein Y is Cl, Br or I and the other groups have the meaning as described above and, if desired, converting the compounds obtained into pharmaceutically acceptable acid addition salts;

The preparation of compounds of formula I of the present invention may be carried out in sequential or convergent synthetic routes. Syntheses of the compounds of the invention are shown in the following schemes. The skills required for carrying out the reaction and purification of the resulting products are known to those skilled in the art. The substituents and indices used in the following description of the processes have the significance given herein before unless indicated to the contrary.

In more detail, the compounds of formula I can be manufactured by the methods given below, by the methods given in the examples or by analogous methods. Appropriate reaction conditions for the individual reaction steps are known to a person skilled in the art. The reaction sequence is not limited to the one displayed in the schemes, however, depending on the starting materials and their respective reactivity the sequence of reaction steps can be freely altered. Starting materials are either commercially available or can be prepared by methods analogous to the methods given below, by methods described in the examples, or by methods known in the art.

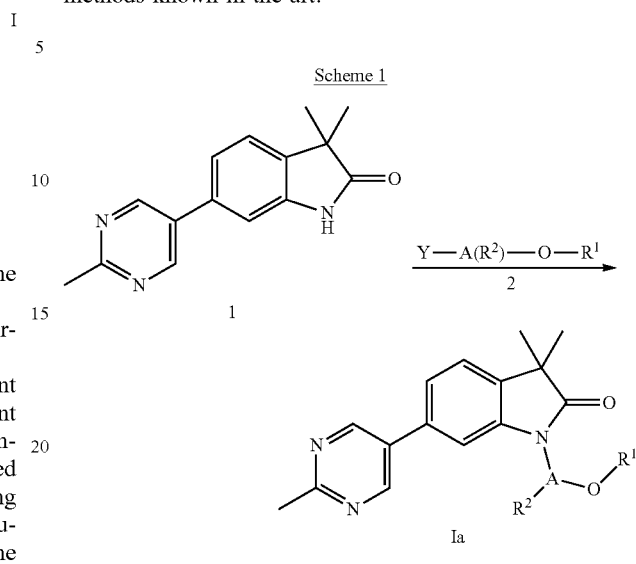

Compounds of formula Ia with A=substituted pyrimidines, pyridines, pyrazines, pyridazines, phenyls and fused rings can be prepared by coupling compounds 1 (WO2014/202493 A1) with aryl-halogenides 2 (Y=Cl, Br, I) in the presence of copper(I)iodide, a ligand such as N,N'-dimethylethylendiamine and a base, e.g. potassium carbonate.

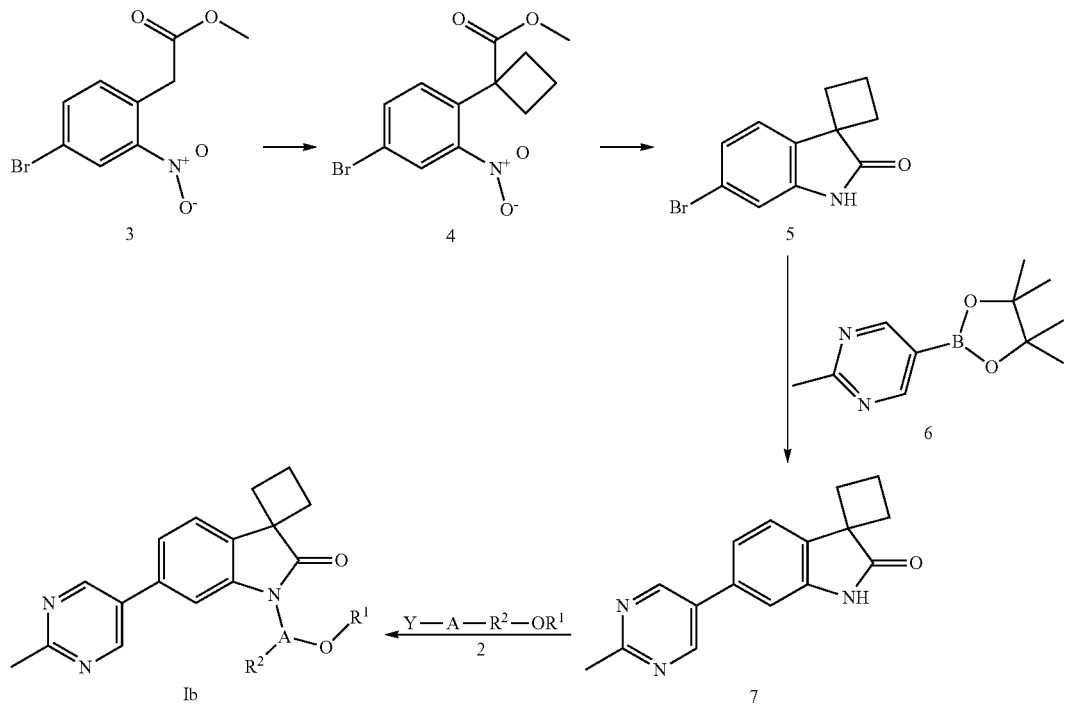

Compounds of formula Ib can be prepared by introduction of the cyclobutyl on methyl 2-(4-bromo-2-nitrophenyl)acetate 3 with 1,3-diiodopropane, followed by intramolecular cyclisation of 4 in presence of iron powder and acetic acid.

Compounds 5 can be coupled with boronic esters 6 in the presence of a palladium catalyst, e.g [1,1'-bis(diphenylphosphino)ferrocene]dichloropalladium(II) and a base, e.g. sodium carbonate to give arylated compound 7. Introduction of the aryl residue A can be accomplished by coupling compound 7 with aryl-halogenides 2 (Y=Cl, Br, I) in the presence of copper(I)iodide, a ligand such as N,N'-dimethylethylendiamine and a base, e.g. potassium carbonate to give compounds of formula Ib.

Experimental Part

The following examples are provided for illustration of the invention. They should not be considered as limiting the scope of the invention, but merely as being representative thereof.

Abbreviations

Boc, t-butyloxycarbonyl;
DIPEA, diisopropylethylamine;
DMAP, dimethylaminopyridine;
DMF, dimethylformamide;
DMSO, dimethylsulfoxide;
EDCI, 1-ethyl-3-(3-dimethylaminopropyl)carb odiimid;
EtOAc, ethyl acetate;
HOBt, 1-hydroxybenzotriazole;
MeOH, methanol;
NMP, N-methyl-2-pyrrolidon;
PMB, p-methoxybenzyl;
TFA, trifluoroacetic acid;
THF, tetrahydrofuran.
General:
Silica gel chromatography was either performed using cartridges packed with silica gel (ISOLUTE® Columns, TELOSTM Flash Columns) or silica-NH2 gel (TELOSTM Flash NH2 Columns) on ISCO Combi Flash Companion or on glass columns on silica gel 60 (32-60 mesh, 60 Å). MS: Mass spectra (MS) were measured with ion spray positive or negative method on a Perkin-Elmer SCIEX API 300.

EXAMPLE 1

1-(6-Methoxypyrazin-2-yl)-3,3-dimethyl-6-(2-methylpyrimidin-5-yl)indolin-2-one

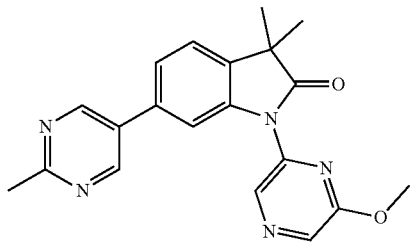

In a microwave tube, a mixture of 3,3-dimethyl-6-(2-methylpyrimidin-5-yl)indolin-2-one (100 mg, 395 µmol, Eq: 1.00, WO2014/202493 A1) and 2-bromo-6-methoxypyrazine (89.5 mg, 474 mol, Eq: 1.2) was mixed in acetonitrile (3 ml). The solvent was degassed by bubbling nitrogen through the suspension for 10 minutes. Then potassium carbonate (136 mg, 987 µmol, Eq: 2.5) was added at 22° C. followed by copper (I) iodide (7.52 mg, 39.5 µmol, Eq: 0.1) and N,N'-dimethylethylenediamine (6.96 mg, 8.5 µl, 79.0 µmol, Eq: 0.2). The tube was inerted, sealed and reacted in microwave at 120° C. for 30 minutes. The mixture was partitioned between ethyl acetate (2 mL) and water (2 mL), the aqueous layer was extracted with ethyl acetate (2×1 mL). The combined organic phase was washed with brine, dried over sodium sulfate, filtered and concentrated in vacuo.

The residue was purified by chromatography on silica gel to afford the desired product as a white solid (110 mg, 77%). MS (m/z)=362.2 [M+H]+.

EXAMPLE 2

1-(5-Methoxypyridin-3-yl)-3,3-dimethyl-6-(2-methylpyrimidin-5-yl)indolin-2-one

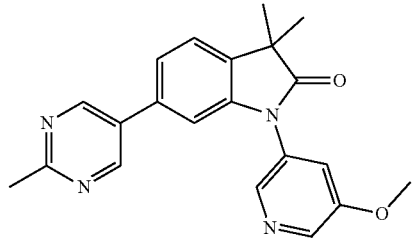

In a pressure tube, a suspension of 3,3-dimethyl-6-(2-methylpyrimidin-5-yl)indolin-2-one (0.15 g, 592 µmol, Eq: 1, WO2014/202493 A1), 3-bromo-5-methoxypyridine (167 mg, 888 µmol, Eq: 1.5) and potassium carbonate (180 mg, 1.3 mmol, Eq: 2.2) in acetonitrile (2.69 ml) was flushed with argon for 5 minutes. Then N,N'-dimethylethylenediamine (21.1 mg, 25.8 µl, 237 µmol, Eq: 0.4) and copper (I) iodide (22.6 mg, 118 µmol, Eq: 0.2) were added and flushing was continued for 1 minute. The tube was sealed and the reaction was heated to 125° C. for 24 h. The reaction was diluted with dichloromethane.

The residue was purified by chromatography on silica gel to afford the desired product as a light brown foam (225 mg, 100%). MS (m/z)=361.2 [M+H]+.

EXAMPLE 3

1-(5-Methoxy-6-methylpyridin-3-yl)-3,3-dimethyl-6-(2-methylpyrimidin-5-yl)indolin-2-one

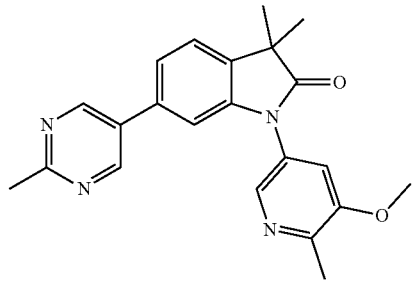

Example 3 was prepared from 3,3-dimethyl-6-(2-methylpyrimidin-5-yl)indolin-2-one (from WO2014/202493 A1)

with 5-bromo-3-methoxy-2-methylpyridine in analogy to example 2 to give the title compound (80%) as a white foam. MS (m/z)=375.2 [(M+H)+].

EXAMPLE 4

1-(2,6-Dimethoxypyrimidin-4-yl)-3,3-dimethyl-6-(2-methylpyrimidin-5-yl)indolin-2-one

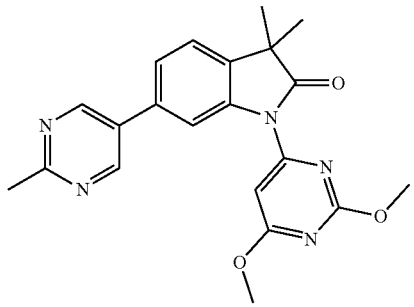

Example 4 was prepared from 3,3-dimethyl-6-(2-methylpyrimidin-5-yl)indolin-2-one (from WO2014/202493 A1) with 4-bromo-2,6-dimethoxypyrimidine in analogy to example 2 to give the title compound (74%) as a white solid. MS (m/z)=392.2 [(M+H)+].

EXAMPLE 5

1-(5-Ethoxypyridin-3-yl)-3,3-dimethyl-6-(2-methyl-pyrimidin-5-yl)indolin-2-one

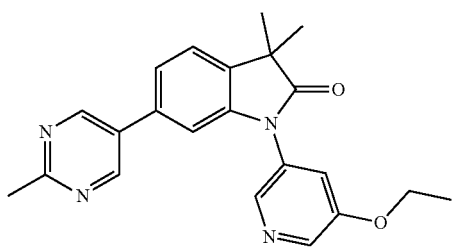 [SMILES: CCOc1cncc(N2C(=O)C(C)(C)c3ccc(-c4cnc(C)nc4)cc32)c1]

Example 5 was prepared from 3,3-dimethyl-6-(2-methylpyrimidin-5-yl)indolin-2-one (from WO02014/202493 A1) with 3-bromo-5-ethoxypyridine in analogy to example 2 to give the title compound (100%) as a white solid. MS (m/z)=375.2 [(M+H)+].

EXAMPLE 6

1-(3-Methoxyphenyl)-3,3-dimethyl-6-(2-methylpyrimidin-5-yl)indolin-2-one

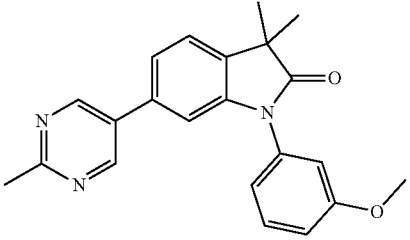

Example 6 was prepared from 3,3-dimethyl-6-(2-methyl-pyrimidin-5-yl)indolin-2-one (from WO2014/202493 A1) with 3-bromoanisole in analogy to example 2 to give the title compound (99%) as a white solid. MS (m/z)=360.2 [(M+H)+].

EXAMPLE 7

1-(5-Isopropoxypyridin-3-yl)-3,3-dimethyl-6-(2-methylpyrimidin-5-yl)indolin-2-one

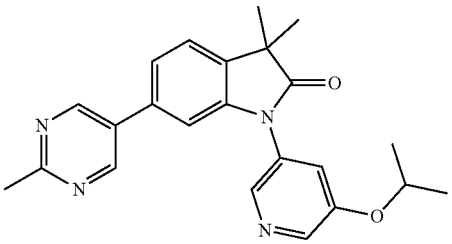 [SMILES: Cc1ncc(-c2ccc3c(c2)N(c2cncc(OC(C)C)c2)C(=O)C3(C)C)cn1]

Example 7 was prepared from 3,3-dimethyl-6-(2-methyl-pyrimidin-5-yl)indolin-2-one (from WO2014/202493 A1) with 3-bromo-5-isopropoxypyridine in analogy to example 2 to give the title compound (89%) as an off-white solid. MS (m/z)=389.2 [(M+H)+].

EXAMPLE 8

1-(3,4-Dihydro-2H-pyrido[3,2-b][1,4]oxazin-7-yl)-3,3-dimethyl-6-(2-methylpyrimidin-5-yl)indolin-2-one

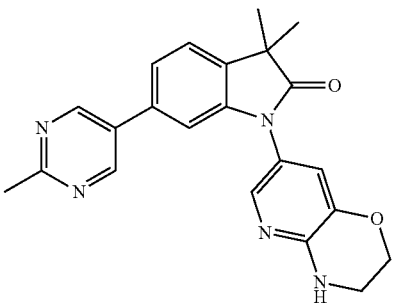 [SMILES: Cc1ncc(-c2ccc3c(c2)N(c2cnc4c(c2)OCCN4)C(=O)C3(C)C)cn1]

Example 8 was prepared from 3,3-dimethyl-6-(2-methylpyrimidin-5-yl)indolin-2-one (from WO2014/202493 A1) with 7-bromo-3,4-dihydro-2H-pyrido[3,2-b][1,4]oxazine in analogy to example 2 to give the title compound (82%) as a light yellow solid. MS (m/z)=388.2 [(M+H)+].

EXAMPLE 9

1-(6-Chloro-5-methoxypyridin-3-yl)-3,3-dimethyl-6-(2-methylpyrimidin-5-yl)indolin-2-one

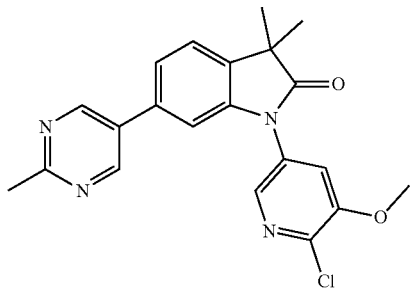

Example 9 was prepared from 3,3-dimethyl-6-(2-methylpyrimidin-5-yl)indolin-2-one (from WO2014/202493 A1) with 5-bromo-2-chloro-3-methoxypyridine in analogy to example 2 to give the title compound (44%) as a white solid. MS (m/z)=395.2 [(M+H)+].

EXAMPLE 10

1-(6-Cyclopropyl-5-methoxypyridin-3-yl)-3,3-dimethyl-6-(2-methylpyrimidin-5-yl)indolin-2-one

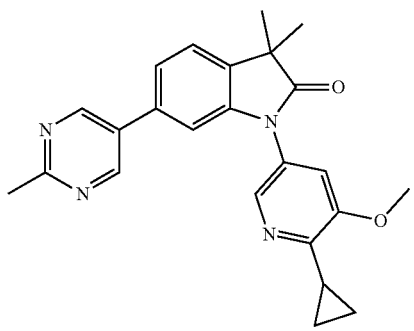

a) 5-Bromo-3-methoxypyridin-2-amine

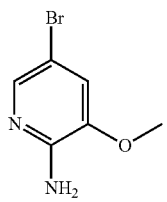

To a solution of 3-methoxypyridin-2-amine (5 g, 40.3 mmol) in acetic acid (50 ml) was added bromine (1N in acetic acid, 40 ml, 40.28 mmol) and the mixture stirred at 25° C. for 16 h. After completion, the reaction mixture was concentrated under vacuum and azeotroped by toluene. The residue thus obtained was neutralized (pH-7) by saturated aqueous sodium bicarbonate solution (70 ml) and extracted with ethyl acetate (2×100 ml). The combined organic layer was dried over anhydrous sodium sulfate and concentrated under vacuum.

The residue was purified by chromatography on silica gel to afford the desired product as a yellow solid (5.6 g, 74%). MS (m/z)=202.8 [M+H]+.

b) 2,5-Dibromo-3-methoxypyridine

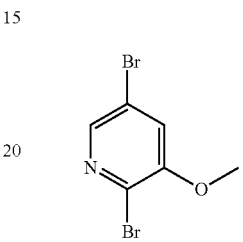

To a solution of 5-bromo-3-methoxypyridin-2-amine (5.5 g, 27.08 mmol) in hydrogen bromide (aq. 47%, 56 ml, 325.06 mmol) was added bromine (4.5 ml, 86.68 mmol) at 0° C. followed by the addition of sodium nitrite (aq. 40%, 23.4 ml, 135.44 mmol) over 20 min and the mixture stirred at 0° C. for 1 h. The reaction mixture was then basified (pH-13) by a 50% aqueous sodium hydroxide solution and allowed to warm up to 25° C. over 1 h. Toluene (100 ml) was then added to the reaction mixture, stirred for 30 min and allowed to stand for 16 h. After completion, the reaction mixture was separated and the aqueous layer was extracted with ethyl acetate (2×50 ml). The combined organic layers were dried over anhydrous sodium sulfate and concentrated under vacuum.

The residue was purified by chromatography on silica gel to afford the desired product as a yellow solid (5.5 g, 76%). MS (m/z)=268.0 [M+H]+.

c) 5-Bromo-2-cyclopropyl-3-methoxypyridine

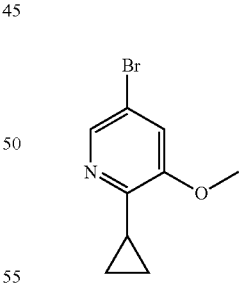

To a stirred solution of 2,5-dibromo-3-methoxypyridine (3.5 g, 13.11 mmol) in toluene (40 ml) and water (10 ml) tripotassium phosphate (8.35 g, 39.34 mmol), potassium cyclopropyltrifluoroborate (2.426 g, 16.39 mmol) were added and purged with argon. Then tetrakis(tripbenylpbosphine)palladium(0) (1.364 g, 1.18 mmol) was added, purged with argon and heated at 100° C. for 16 h. The reaction mixture was filtered and concentrated under vacuum. The residue was purified by chromatography on silica gel to afford the desired product as a light yellow liquid (700 mg, 55%). MS (m/z)=227.6 [M+H]+.

d) 1-(6-Cyclopropyl-5-methoxypyridin-3-yl)-3,3-dimethyl-6-(2-methylpyrimidin-5-yl)indolin-2-one

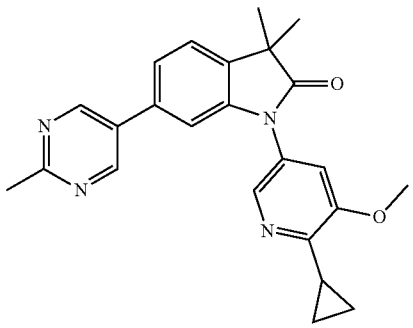

Example 10d was prepared from 3,3-dimethyl-6-(2-methylpyrimidin-5-yl)indolin-2-one (from WO2014/202493 A1) with 5-bromo-2-cyclopropyl-3-methoxypyridine in analogy to example 2 to give the title compound (99%) as a white foam. MS (m/z)=401.2 [(M+H)$^+$].

EXAMPLE 11

1-(5-Methoxypyrazin-2-yl)-3,3-dimethyl-6-(2-methylpyrimidin-5-yl)indolin-2-one

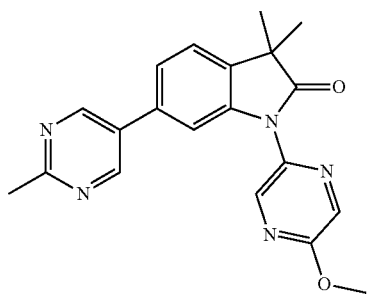

Example 11 was prepared from 3,3-dimethyl-6-(2-methylpyrimidin-5-yl)indolin-2-one (from WO2014/202493 A1) with 2-bromo-5-methoxypyrazine in analogy to example 2 to give the title compound (75%) as a white solid. MS (m/z)=362.2 [(M+H)$^+$].

EXAMPLE 12

1-(6-Methoxypyridazin-3-yl)-3,3-dimethyl-6-(2-methylpyrimidin-5-yl)indolin-2-one

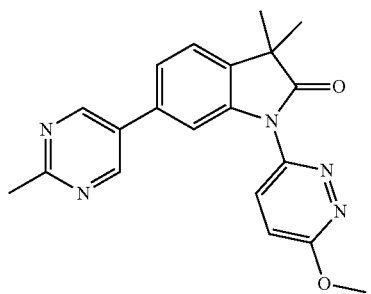

Example 12 was prepared from 3,3-dimethyl-6-(2-methylpyrimidin-5-yl)indolin-2-one (from WO02014/202493 A1) with 3-bromo-6-methoxypyridazine in analogy to example 2 to give the title compound (82%) as a white solid. MS (m/z)=362.1 [(M+H)$^+$].

EXAMPLE 13

1-(6-Hydroxypyridazin-3-yl)-3,3-dimethyl-6-(2-methylpyrimidin-5-yl)indolin-2-one

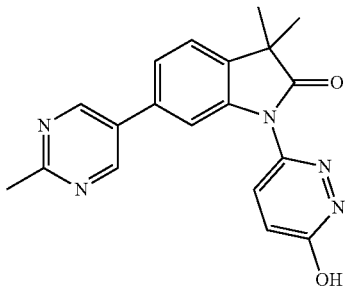 [SMILES: Cc1ncc(-c2ccc3c(c2)N(c2ccc(O)nn2)C(=O)C3(C)C)cn1]

1-(6-Methoxypyridazin-3-yl)-3,3-dimethyl-6-(2-methylpyrimidin-5-yl)indolin-2-one (18 mg, 49.8 μmol, Eq: 1, Example 12) was diluted in hydrobromic acid, 48% aq. (8.4 mg, 5.63 μl, 49.8 μmol, Eq: 1) and the reaction mixture was heated to 110° C. and stirred for 2 h. The mixture was concentrated in vacuo. The residue was purified by preparative HPLC to afford the desired product as a colorless oil (7 mg, 40%). MS (m/z)=348.3 [M+H]+.

EXAMPLE 14

3,3-Dimethyl-6-(2-methylpyrimidin-5-yl)-1-(5-(trifluoromethoxy)pyridin-2-yl)indolin-2-one

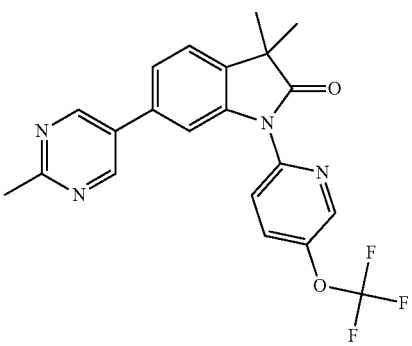 [SMILES: Cc1ncc(-c2ccc3c(c2)N(c2ccc(OC(F)(F)F)cn2)C(=O)C3(C)C)cn1]

Example 14 was prepared from 3,3-dimethyl-6-(2-methylpyrimidin-5-yl)indolin-2-one (from WO2014/202493 A1) with 2-bromo-5-(trifluoromethoxy)pyridine in analogy to example 2 to give the title compound (96%) as a white solid. MS (m/z)=415.1 [(M+H)$^+$].

EXAMPLE 15

1-(2-Methoxypyrimidin-5-yl)-3,3-dimethyl-6-(2-methylpyrimidin-5-yl)indolin-2-one

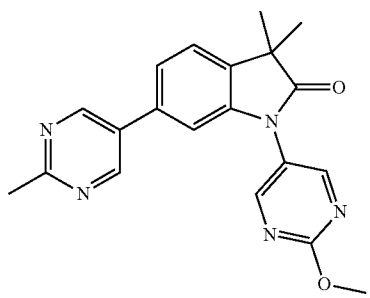

Example 15 was prepared from 3,3-dimethyl-6-(2-methylpyrimidin-5-yl)indolin-2-one (from WO2014/202493 A1) with 5-bromo-2-methoxypyrimidine in analogy to example 2 to give the title compound (76%) as a white solid. MS (m/z)=362.2 [(M+H)+].

EXAMPLE 16

3,3-Dimethyl-6-(2-methylpyrimidin-5-yl)-1-(6-(2,2,2-trifluoroethoxy)pyridin-3-yl)indolin-2-one

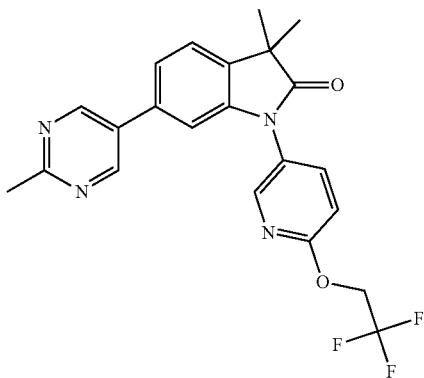 [SMILES: Cc1ncc(-c2ccc3c(c2)N(c2ccc(OCC(F)(F)F)nc2)C(=O)C3(C)C)cn1]

Example 16 was prepared from 3,3-dimethyl-6-(2-methylpyrimidin-5-yl)indolin-2-one (from WO2014/202493 A1) with 5-bromo-2-(2,2,2-trifluoroethoxy)pyridine in analogy to example 2 to give the title compound (99%) as a light yellow foam. MS (m/z)=429.2 [(M+H)+].

EXAMPLE 17

3,3-Dimethyl-6-(2-methylpyrimidin-5-yl)-1-(2-(oxetan-3-yloxy)pyrimidin-5-yl)indolin-2-one

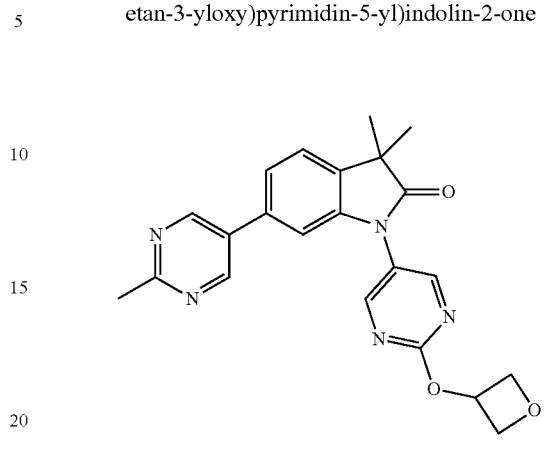

Example 17 was prepared from 3,3-dimethyl-6-(2-methylpyrimidin-5-yl)indolin-2-one (from WO02014/202493 A1) with 5-bromo-2-(oxetan-3-yloxy)pyrimidine in analogy to example 2 to give the title compound (80%) as a white solid. MS (m/z)=404.2 [(M+H)+].

EXAMPLE 18

3,3-Dimethyl-1-(3-methylbenzo[d]isoxazol-5-yl)-6-(2-methylpyrimidin-5-yl)indolin-2-one

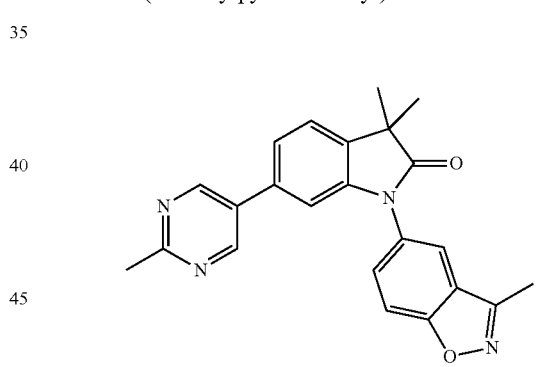

3,3-Dimethyl-6-(2-methylpyrimidin-5-yl)indolin-2-one (100 mg, 395 µmol, Eq: 1, WO2014/202493 A1), 5-bromo-3-methylbenzo[d]isoxazole (111 mg, 513 µmol, Eq: 1.30), copper (I) iodide (7.52 mg, 39.5 µmol, Eq: 0.10), potassium carbonate (109 mg, 790 µmol, Eq: 2.00) and (1R,2R)—N1,N2-dimethylcyclohexane-1,2-diamine (11.6 mg, 12.8 µl, 79 µmol, Eq: 0.20) were combined with degassed dioxane (6 ml) under nitrogen. The reaction mixture was heated to 110° C. and stirred for 24 h under nitrogen atmosphere. The reaction mixture was poured into saturated sodium bicarbonate and extracted with ethyl acetate (2×). The organic layers were combined and washed with water and brine. The organic phase was dried over sodium sulfate and concentrated in vacuo.

The residue was purified by chromatography on silica gel, followed by preparative HPLC to afford the desired product as an off-white solid (12 mg, 7%). MS (m/z)=385.3 [M+H]+.

EXAMPLE 19

1'-(5-Methoxypyridin-3-yl)-6'-(2-methylpyrimidin-5-yl)spiro[cyclobutane-1,3'-indolin]-2'-one

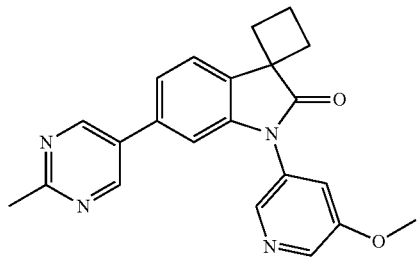

a) Methyl 1-(4-bromo-2-nitrophenyl)cyclobutanecarboxylate

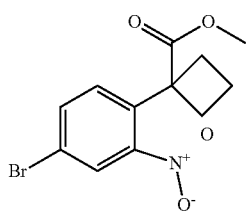

Methyl 2-(4-bromo-2-nitrophenyl)acetate (2 g, 7.3 mmol, Eq: 1) and 1,3-diiodopropane (2.45 g, 956 µl, 8.03 mmol, Eq: 1.10) were combined with dimethylformamide (20 ml) at 0° C. Sodium hydride (1.17 g, 29.2 mmol, Eq: 4.00) was slowly added. The dark blue reaction mixture was heated to room temperature and stirred for 16 h. The reaction mixture was poured into water and extracted with ethyl acetate (3×). The organic layers were combined and washed with brine, dried over sodium sulfate, filtered and concentrated in vacuo.

The residue was purified by chromatography on silica gel to afford the desired product as a brown solid (285 mg, 12%).

b) 6'-Bromospiro[cyclobutane-1,3'-indolin]-2'-one

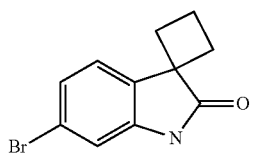

Methyl 1-(4-bromo-2-nitrophenyl)cyclobutanecarboxylate (285 mg, 907 µmol, Eq: 1) was combined with acetic acid (3 ml). Iron powder (253 mg, 4.54 mmol, Eq: 5.00) was added. The reaction mixture was heated to 100° C. and stirred for 2 h. The reaction mixture was filtered through celite and the filtrate was evaporated.

The residue was purified by chromatography on silica gel to afford the desired product as a brown solid (130 mg, 56%). MS (m/z)=254.1 [M+H]+.

c) 6'-(2-Methylpyrimidin-5-yl)spiro[cyclobutane-1,3'-indolin]-2'-one

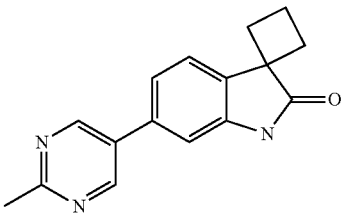 [SMILES: Cc1ncc(-c2ccc3c(c2)NC(=O)C32CCC2)cn1]

6'-Bromospiro[cyclobutane-1,3'-indolin]-2'-one (120 mg, 476 µmol, Eq: 1), 2-methyl-5-(4,4,5,5-tetramethyl-1,3,2-dioxaborolan-2-yl)pyrimidine (157 mg, 714 µmol, Eq: 1.50) and dichlor(1,1'-bis(diphenylphosphino)ferrocene)palladium (II) dichloromethane adduct (19.4 mg, 23.8 µmol, Eq: 0.05) were combined with a degassed solution 2M of sodium carbonate (714 µl, 1.43 mmol, Eq: 3.00) and degassed dioxane (4 ml) under nitrogen atmosphere. The reaction mixture was heated to 110° C. and stirred for 24 h. The reaction mixture was poured into saturated sodium bicarbonate and extracted with ethyl acetate (3×). The organic layers were combined and washed with brine, dried over sodium sulfate, filtered and concentrated in vacuo.

The residue was purified by chromatography on silica gel to afford the desired product as a light brown solid (100 mg, 79%). MS (m/z)=266.2 [M+H]+.

d) 1'-(5-Methoxypyridin-3-yl)-6'-(2-methylpyrimidin-5-yl)spiro[cyclobutane-1,3'-indolin]-2'-one

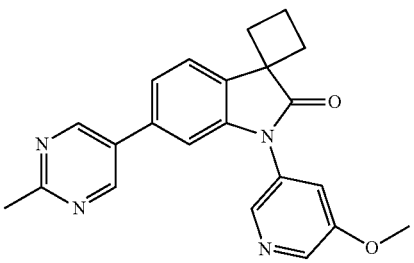

Example 19d was prepared from 6'-(2-methylpyrimidin-5-yl)spiro[cyclobutane-1,3'-indolin]-2'-one with 3-bromo-5-methoxypyridine in analogy to example 18 to give the title compound (90%) as a light brown solid. MS (m/z)=373.3 [(M+H)+].

EXAMPLE 20

1'-(6-Methoxypyridazin-3-yl)-6'-(2-methylpyrimidin-5-yl)spiro[cyclobutane-1,3'-indolin]-2'-one

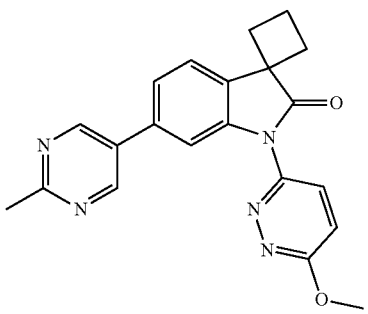

Example 20 was prepared from 6'-(2-methylpyrimidin-5-yl)spiro[cyclobutane-1,3'-indolin]-2'-one (Example 19c) with 3-bromo-6-methoxypyridazine in analogy to example 18 to give the title compound (71%) as a light brown solid. MS (m/z)=374.2 [(M+H)$^+$].

Biological Assays and Data

Now it has been found that the compounds of formula I may be used for the treatment of CNS diseases.

The described compounds of formula I reduce L-687,414-induced hyperlocomotion. This was assessed by using a computerized Digiscan 16 Animal Activity Monitoring System (Omnitech Electronics, Columbus, Ohio) to quantify locomotor activity. Animals were kept under a 12 h light/dark cycle and experiments were performed during the light period. Each activity monitoring chamber consisted of a Plexiglas box (41×41×28 cm; W×L×H) with sawdust bedding on the floor surrounded by invisible horizontal and vertical infrared sensor beams. The test boxes were divided by a Plexiglas cross providing each mouse with 20×20 cm of moving space. Cages were connected to a Digiscan Analyzer linked to a computer that constantly collected the beam status information. Records of photocell beam interruptions for individual animals were taken every 5 min over the duration of the experimental session and the sum of the first 6 periods was used as the final parameter. At least 8 mice were used in each treatment group. Compounds were administered i.p 15 min before a s.c. injection of 50 mg/kg of L-687,414. Mice were then transferred from their home cage to the recording chambers for a 15-min habituation phase allowing free exploration of the new environment. Horizontal activity was then recorded for a 30-min time period. The % inhibition of L-687,414-induced hyperlocomotion was calculated according to the equation:

((Veh+L−687,414 horizontal activity−drug+L−687,414 horizontal activity)/Veh+L−687,414 horizontal activity)×100

ID$_{50}$ values, defined as doses of each compound producing 50% inhibition of L-687,414-induced hyperlocomotion, were calculated by linear regression analysis of a dose-response data using an Excel-based computer-fitting program.

As data was not presupposed to be normally distributed, groups treated with test compounds were statistically compared with the control (vehicle-treated) group using one-tailed Mann Whitney U tests. In statistics, the Mann-Whitney Utest (also called the Mann-Whitney-Wilcoxon (MWW) or Wilcoxon rank-sum test) is a non-parametric statistical hypothesis test for assessing whether one of two samples of independent observations tends to have larger values than the other. It is one of the most well-known non-parametric significance tests. A p value gives the probability that two groups are significantly different from each other and the value of <0.05 is generally accepted as a criterion, it implies that there is >95% chance that two groups are really different from each other. P values given in table 1 are one-tailed since only decreases in locomotion were expected and tested for (Mann, H. B., Whitney, D. R. (1947), "On a Test of Whether one of Two Random Variables is Stochastically Larger than the Other", Annals of Mathematical Statistics, 18 (1), 50-60).

Determination of Adenosine Transport Activity

To measure adenosine transport activity of ENT-1 mammalian cells, stable cells expressing the mouse ENT-1 transporter were plated on day 1 in 96-well culture plates at the density of 60,000 cells/well, in complete DMEM/F12 medium supplemented with glutamax, 10% FBS and 10 μg/ml puromycin. On day 2, the medium was aspirated and the cells were washed twice with uptake buffer (10 mM Hepes-Tris, pH 7.4 containing 150 mM NaCl, 1 mM CaCl$_2$, 2.5 mM KCl, 2.5 mM MgSO$_4$, 10 mM D-glucose) (UB). For inhibition experiments, cells were then incubated at RT with various concentrations of compounds with 1% DMSO final. Non-specific uptake was defined in the presence of 10 μM S-(4-Nitrobenzyl)-6-thioinosine (NBTI, Sigma Cat #N2255).

A solution containing [2,8-$^3$H]-adenosine 6 nM (40 Ci/mmol, American Radiolabeled chemicals Inc, Cat #ART 0287A) was then immediately added to the wells. The plates were then incubated for 20 min with gentle shaking and the reaction was stopped by aspiration of the mixture and washing (three times) with ice-cold UB. The cells were lysed by the addition of scintillation liquid, shaken 3 hours and the radioactivity in the cells was estimated using a microplates scintillation counter (TopCount NXT, Packard).

TABLE 1

Effects of compounds of formula I on ENT1 inhibition

| Expl. | structure | ENT1, adenosine uptake, IC50 (uM) |
|---|---|---|
| 1 | 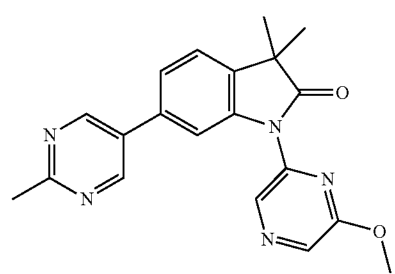 | 0.073 |

TABLE 1-continued

Effects of compounds of formula I on ENT1 inhibition

| Expl. | structure | ENT1, adenosine uptake, IC50 (uM) |
|---|---|---|
| 2 | 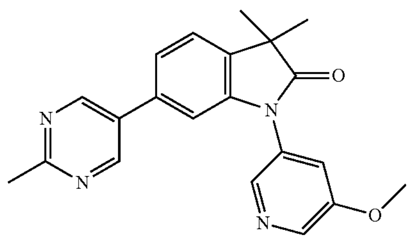 | 0.4379 |
| 3 | 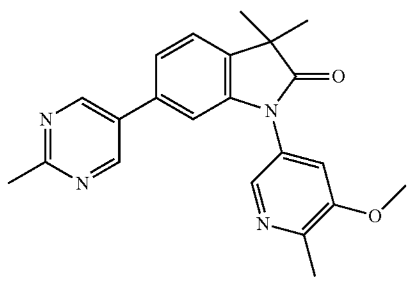 | 0.2422 |
| 4 | 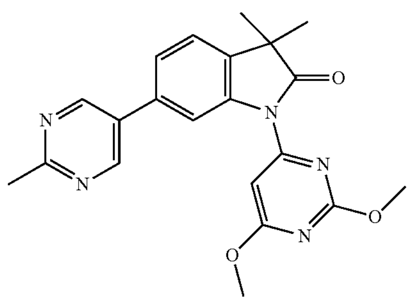 | 0.1098 |
| 5 | 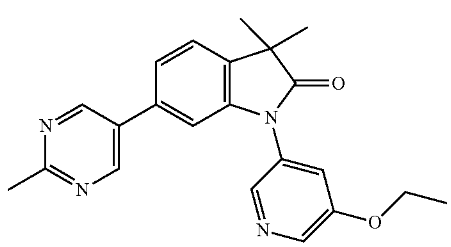 [SMILES: CCOc1cncc(N2C(=O)C(C)(C)c3ccc(-c4cnc(C)nc4)cc32)c1] | 0.0643 |
| 6 | 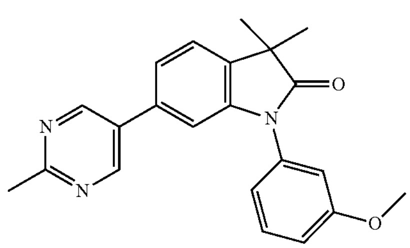 | 0.2889 |
| 7 | 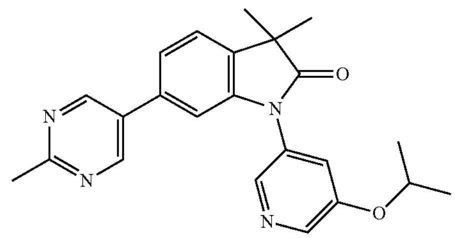 [SMILES: Cc1ncc(-c2ccc3c(c2)N(c2cncc(OC(C)C)c2)C(=O)C3(C)C)cn1] | 0.1835 |
| 8 | 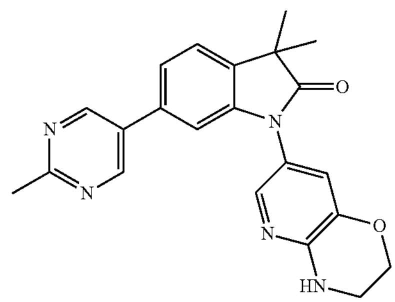 [SMILES: Cc1ncc(-c2ccc3c(c2)N(c2cnc4c(c2)OCCN4)C(=O)C3(C)C)cn1] | 0.9511 |
| 9 | 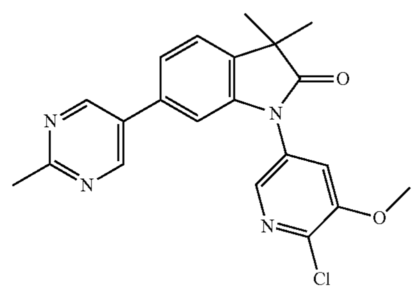 | 0.1544 |
| 10 | 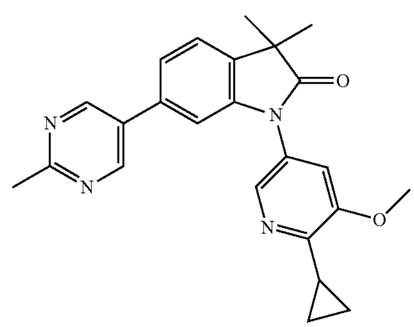 | 0.1394 |
| 11 | 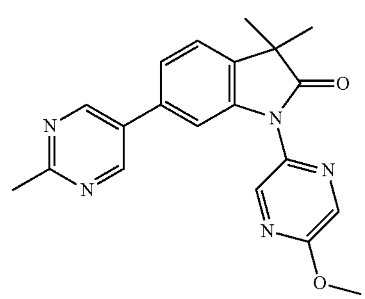 | 0.2723 |

TABLE 1-continued

Effects of compounds of formula I on ENT1 inhibition

| Expl. | structure | ENT1, adenosine uptake, IC50 (uM) |
|---|---|---|
| 12 | 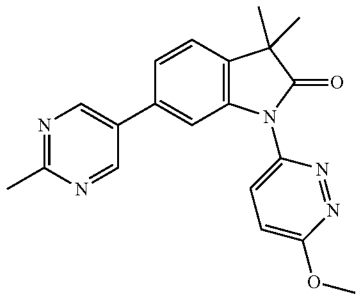 | 0.0348 |
| 13 | 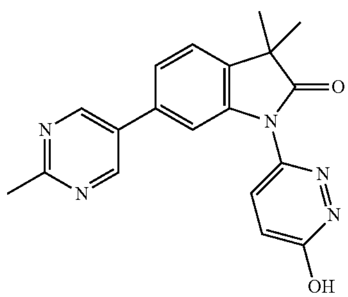 [SMILES: Cc1ncc(-c2ccc3c(c2)N(c2ccc(O)nn2)C(=O)C3(C)C)cn1] | 0.6155 |
| 14 | 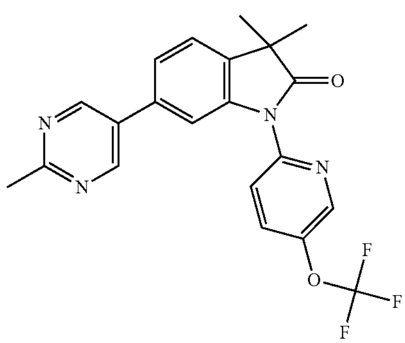 [SMILES: Cc1ncc(-c2ccc3c(c2)N(c2ccc(OC(F)(F)F)cn2)C(=O)C3(C)C)cn1] | 0.1182 |
| 15 | 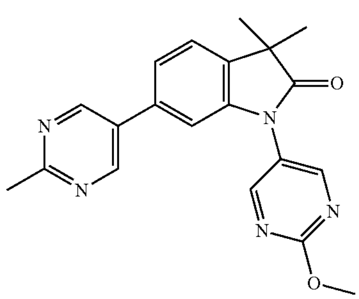 | 0.8431 |
| 16 | | 0.8106 |
| 17 | | 0.8227 |
| 18 | | 0.0509 |
| 19 | | 0.7845 |

TABLE 1-continued

Effects of compounds of formula I on ENT1 inhibition

| Expl. | structure | ENT1, adenosine uptake, IC50 (uM) |
|---|---|---|
| 20 | 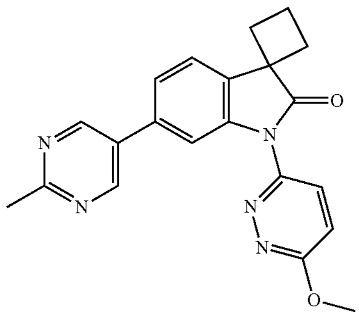 | 0.1302 |

TABLE 2

Effects on compounds for L-687,414-induced hyperlocomotion

| | | L-687,414-induced hyperlocomotion | |
|---|---|---|---|
| Expl. | Dose ip [mg/kg] | Inhibition, ip [%] | P value |
| 2 | 30 ip | 93.6 | 0.00016 |
| 12 | 30 ip | 94.6 | 0.00008 |

As mentioned above, some compounds have been tested in SmartCube®, an analytical system developed by Psycho-Genics Inc.

SmartCube® was used to compare the behavioral signature of a test compound to a database of behavioral signatures obtained from a large set of clinically approved reference drugs, grouped per indications. In this way, the neuropharmacological effects of a test compound can be predicted by similarity to major classes of compounds, such as antipsychotics, anxiolytics and antidepressants. This approach is ideally suited to screen collections of existing drugs or drug candidates with previously unknown neuropharmacology, which could expedite the development of new and unexpected treatments for psychiatric disorders.

Some compounds of the present invention were injected i.p. at different doses 15 minutes before the test. At least 8 mice were used in each treatment group. Digital videos of the subjects were processed with computer vision algorithms to extract over 2000 dependent measures including frequency and duration of many different behavioral states. The results of the classifications are presented as bar charts for each compound and dose (mg/kg), the Y-axis indicates the relative probability that the test compound will show efficacy in the specific CNS indication.

Compounds of the present invention show similar signatures to those of atypical antipsychotics. An independent analysis was performed on the unclassified data to determine the similarity of the example compounds to active doses of known atypical antipsychotics. For this analysis, we use discrimination rate as the measure of separability between the two drugs, i.e. one drug's "distinguishability" from another. A rate equal to 50% (or 0.5) corresponds to zero distinguishability. Empirical data has shown that a threshold rate for reliable separation lies above 70% i.e., two drugs showing a discrimination rate of 70% or lower are considered similar, whereas a discrimination rate higher than 70% indicates that two drugs are dissimilar. The table below shows the similarity analysis of selected compounds of the present invention to several atypical antipsychotics. In most cases, the example compounds show a similarity to risperidone, clozapine and olanzapine with a discrimination rate of ≤0.70.

TABLE 3

Similarity analysis of compounds of formula I (at 3 mg/kg) showing effects in SmartCube ®

| Example | Clozapine (1.0 mg/kg) | Olanzapine (0.25 mg/kg) | Risperidone (0.06 mg/kg) |
|---|---|---|---|
| 2 | 0.58 | 0.68 | 0.51 |
| 12 | 0.67 | 0.63 | 0.56 |

Therefore, it can be assumed that the present compounds have similar efficacies as known atypical antipsychotics.

The compounds of formula (I) and pharmaceutically acceptable salts thereof can be used as medicaments, e.g. in the form of pharmaceutical preparations. The pharmaceutical preparations can be administered orally, e.g. in the form of tablets, coated tablets, dragées, hard and soft gelatine capsules, solutions, emulsions or suspensions. However, the administration can also be effected rectally, e.g. in the form of suppositories, or parenterally, e.g. in the form of injection solutions.

The compounds of formula (I) and pharmaceutically acceptable salts thereof can be processed with pharmaceutically inert, inorganic or organic carriers for the production of pharmaceutical preparations. Lactose, corn starch or derivatives thereof, talc, stearic acid or its salts and the like can be used, for example, as such carriers for tablets, coated tablets, dragées and hard gelatine capsules. Suitable carriers for soft gelatine capsules are, for example, vegetable oils, waxes, fats, semi-solid and liquid polyols and the like; depending on the nature of the active substance no carriers are, however, usually required in the case of soft gelatine capsules. Suitable carriers for the production of solutions and syrups are, for example, water, polyols, sucrose, invert sugar, glucose and the like. Adjuvants, such as alcohols, polyols, glycerol, vegetable oils and the like, can be used for aqueous injection solutions of water-soluble salts of compounds of formula (I), but as a rule are not necessary. Suitable carriers for suppositories are, for example, natural or hardened oils, waxes, fats, semi-liquid or liquid polyols and the like.

In addition, the pharmaceutical preparations can contain preservatives, solubilizers, stabilizers, wetting agents, emulsifiers, sweeteners, colorants, flavorants, salts for varying the osmotic pressure, buffers, masking agents or antioxidants. They can also contain still other therapeutically valuable substances.

As mentioned earlier, medicaments containing a compound of formula (I) or pharmaceutically acceptable salts thereof and a therapeutically inert excipient are also an object of the present invention, as is a process for the production of such medicaments which comprises bringing one or more compounds of formula I or pharmaceutically acceptable salts thereof and, if desired, one or more other therapeutically valuable substances into a galenical dosage form together with one or more therapeutically inert carriers. The active compounds may also be used in form of their prodrugs.

As further mentioned earlier, the use of the compounds of formula (I) for the preparation of medicaments useful in the prevention and/or the treatment of the above recited diseases is also an object of the present invention.

The dosage can vary within wide limits and will, of course, be fitted to the individual requirements in each particular case. In general, the effective dosage for oral or parenteral administration is between 0.01-20 mg/kg/day, with a dosage of 0.1-10 mg/kg/day being preferred for all of the indications described. The daily dosage for an adult person weighing 70 kg accordingly lies between 0.7-1400 mg per day, preferably between 7 and 700 mg per day.

Preparation of Pharmaceutical Compositions Comprising Compounds of the Invention Tablets of the following composition are manufactured in the usual manner:

| | mg/tablet | | | |
|---|---|---|---|---|
| ingredient | 5 | 25 | 100 | 500 |
| Compound of formula I | 5 | 25 | 100 | 500 |
| Lactose Anhydrous DTG | 125 | 105 | 30 | 150 |
| Sta-Rx 1500 | 6 | 6 | 6 | 60 |
| Microcrystalline Cellulose | 30 | 30 | 30 | 450 |
| Magnesium Stearate | 1 | 1 | 1 | 1 |
| Total | 167 | 167 | 167 | 831 |

Manufacturing Procedure

1. Mix ingredients 1, 2, 3 and 4 and granulate with purified water.
2. Dry the granules at 50° C.
3. Pass the granules through suitable milling equipment.
4. Add ingredient 5 and mix for three minutes; compress on a suitable press.

Capsules of the following composition are manufactured:

| | mg/capsule | | | |
|---|---|---|---|---|
| ingredient | 5 | 25 | 100 | 500 |
| Compound of formula I | 5 | 25 | 100 | 500 |
| Hydrous Lactose | 159 | 123 | 148 | — |
| Corn Starch | 25 | 35 | 40 | 70 |
| Talk | 10 | 15 | 10 | 25 |
| Magnesium Stearate | 1 | 2 | 2 | 5 |
| Total | 200 | 200 | 300 | 600 |

Manufacturing Procedure

1. Mix ingredients 1, 2 and 3 in a suitable mixer for 30 minutes.
2. Add ingredients 4 and 5 and mix for 3 minutes.
3. Fill into a suitable capsule.

A compound of formula I lactose and corn starch are firstly mixed in a mixer and then in a comminuting machine. The mixture is returned to the mixer; the talc is added thereto and mixed thoroughly. The mixture is filled by machine into suitable capsules, e.g. hard gelatin capsules.

Injection solutions of the following composition are manufactured:

| ingredient | mg/injection solution. |
|---|---|
| Compound of formula I | 3 |
| Polyethylene Glycol 400 | 150 |
| acetic acid | q.s. ad pH 5.0 |
| water for injection solutions | ad 1.0 ml |

Manufacturing Procedure

A compound of formula I is dissolved in a mixture of Polyethylene Glycol 400 and water for injection (part). The pH is adjusted to 5.0 by acetic acid. The volume is adjusted to 1.0 ml by addition of the residual amount of water. The solution is filtered, filled into vials using an appropriate overage and sterilized.

The invention claimed is:

1. A compound of formula

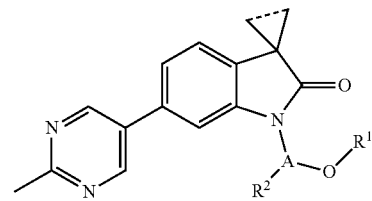

I wherein

A is phenyl or a six membered heteroaryl group, containing one or two N atoms, selected from

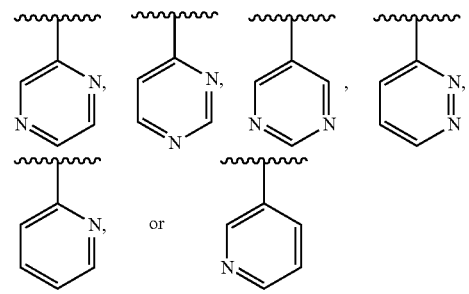

or the oxygen atom may form together with two neighboring carbon atoms from the group A an additional fused ring, selected from

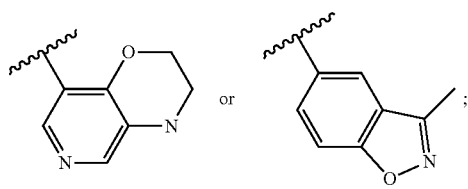 [SMILES: *c1cncc2c1OCCN2 ; *c1ccc2onc(C)c2c1]

$R^1$ is hydrogen, lower alkyl, lower alkyl substituted by halogen or oxetanyl;
$R^2$ is hydrogen, lower alkyl lower alkoxy, halogen or cycloalkyl; and
--- the dotted line is nothing or may be —$CH_2$—;
or a pharmaceutically acceptable salt thereof.

2. A compound of formula IA according to claim 1,

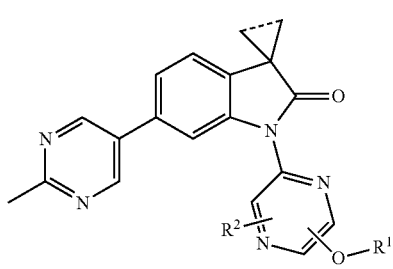

wherein
R¹ is hydrogen, lower alkyl, lower alkyl substituted by halogen or oxetanyl;
R² is hydrogen, lower alkyl lower alkoxy, halogen or cycloalkyl; and
--- the dotted line is nothing or may be —CH₂—;
or a pharmaceutically acceptable salt thereof.

3. A compound of formula IA according to claim 2, which compound is:
  1-(6-methoxypyrazin-2-yl)-3,3-dimethyl-6-(2-methylpyrimidin-5-yl)indolin-2-one; or
  1-(5-methoxypyrazin-2-yl)-3,3-dimethyl-6-(2-methylpyrimidin-5-yl)indolin-2-one, or a pharmaceutically acceptable salt thereof.

4. A compound of formula IB according to claim 1

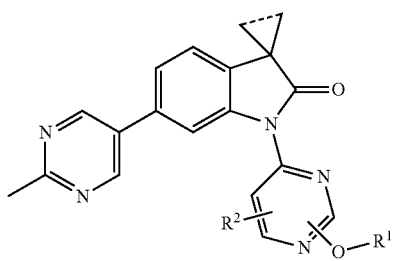

wherein
R¹ is hydrogen, lower alkyl, lower alkyl substituted by halogen or oxetanyl;
R² is hydrogen, lower alkyl lower alkoxy, halogen or cycloalkyl; and
--- the dotted line is nothing or may be —CH₂—;
or a pharmaceutically acceptable salt thereof.

5. A compound of formula IB according to claim 4, which compound is:
  1-(2,6-dimethoxypyrimidin-4-yl)-3,3-dimethyl-6-(2-methylpyrimidin-5-yl)indolin-2-one, or a pharmaceutically acceptable salt thereof.

6. A compound of formula IC according to claim 1,

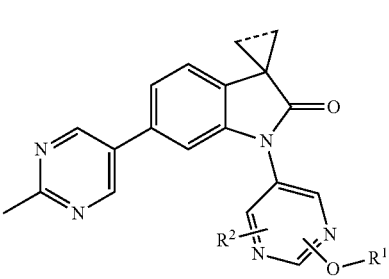

wherein
R¹ is hydrogen, lower alkyl, lower alkyl substituted by halogen or oxetanyl;
R² is hydrogen, lower alkyl lower alkoxy, halogen or cycloalkyl; and
--- the dotted line is nothing or may be —CH₂—;
or a pharmaceutically acceptable salt thereof.

7. A compound of formula IC according to claim 6, which compound is:
  1-(2-methoxypyrimidin-5-yl)-3,3-dimethyl-6-(2-methylpyrimidin-5-yl)indolin-2-one; or
  3,3-dimethyl-6-(2-methylpyrimidin-5-yl)-1-(2-(oxetan-3-yloxy)pyrimidin-5-yl)indolin-2-one, or a pharmaceutically acceptable salt thereof.

8. A compound of formula ID according to claim 1,

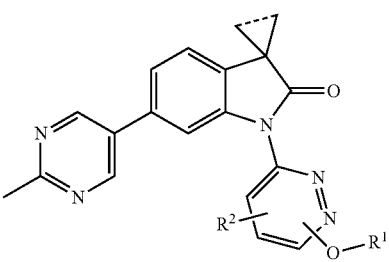

wherein
R¹ is hydrogen, lower alkyl, lower alkyl substituted by halogen or oxetanyl;
R² is hydrogen, lower alkyl lower alkoxy, halogen or cycloalkyl; and
--- the dotted line is nothing or May be —CH₂—;
or a pharmaceutically acceptable salt thereof.

9. A compound of formula ID according to claim 8, which compound is:
  1-(6-methoxypyridazin-3-yl)-3,3-dimethyl-6-(2-methylpyrimidin-5-yl)indolin-2-one;
  1-(6-hydroxypyridazin-3-yl)-3,3-dimethyl-6-(2-methylpyrimidin-5-yl)indolin-2-one; or
  1'-(6-methoxypyridazin-3-yl)-6'-(2-methylpyrimidin-5-yl)spiro[cyclobutane-1,3'-indolin]-2'-one, or a pharmaceutically acceptable salt thereof.

10. A compound of formula IE according to claim 1

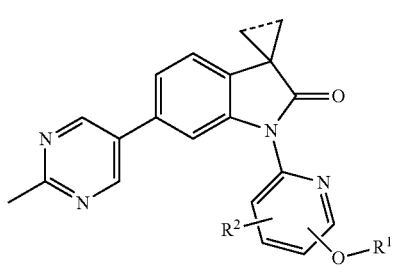

wherein
R¹ is hydrogen, lower alkyl, lower alkyl substituted by halogen or oxetanyl;
R² is hydrogen, lower alkyl lower alkoxy, halogen or cycloalkyl; and
--- the dotted line is nothing or may be —CH₂—;
or a pharmaceutically acceptable salt thereof.

11. A compound of formula IE according to claim 10, which compound is:
3,3-dimethyl-6-(2-methylpyrimidin-5-yl)-1-(5-(trifluoromethoxy)pyridin-2-yl)indolin-2-one, or a pharmaceutically acceptable salt thereof.

12. A compound of formula IF according to claim 1

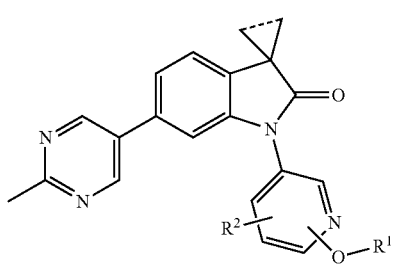

wherein
R¹ is hydrogen, lower alkyl, lower alkyl substituted by halogen or oxetanyl;
R² is hydrogen, lower alkyl lower alkoxy, halogen or cycloalkyl; and
--- the dotted line is nothing or may be —CH₂—;
or a pharmaceutically acceptable salt thereof.

13. A compound of formula IF according to claim 12, which compound is:
1-(5-methoxypyridin-3-yl)-3,3-dimethyl-6-(2-methylpyrimidin-5-yl)indolin-2-one;
1-(5-methoxy-6-methylpyridin-3-yl)-3,3-dimethyl-6-(2-methylpyrimidin-5-yl)indolin-2-one;
1-(5-ethoxypyridin-3-yl)-3,3-dimethyl-6-(2-methylpyrimidin-5-yl)indolin-2-one;
1-(5-isopropoxypyridin-3-yl)-3,3-dimethyl-6-(2-methylpyrimidin-5-yl)indolin-2-one;
1-(6-chloro-5-methoxypyridin-3-yl)-3,3-dimethyl-6-(2-methylpyrimidin-5-yl)indolin-2-one;
1-(6-cyclopropyl-5-methoxypyridin-3-yl)-3,3-dimethyl-6-(2-methylpyrimidin-5-yl)indolin-2-one;
3,3-dimethyl-6-(2-methylpyrimidin-5-yl)-1-(6-(2,2,2-trifluoroethoxy)pyridin-3-yl)indolin-2-one; or
1'-(5-methoxypyridin-3-yl)-6'-(2-methylpyrimidin-5-yl)spiro[cyclobutane-1,3'-indolin]-2'-one, or a pharmaceutically acceptable salt thereof.

14. A compound of formula IG according to claim 1

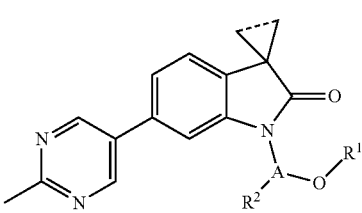

wherein
A is phenyl or

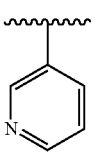

and the oxygen atom may form together with two neighboring carbon atoms from the group A an additional fused ring, selected from

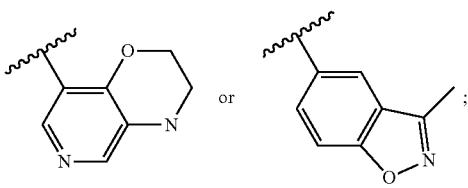 [SMILES: *c1cncc2c1OCCN2 ; *c1ccc2onc(C)c2c1]

R¹ is hydrogen;
R² is hydrogen; and
--- the dotted line is nothing or may be —CH₂—;
or a pharmaceutically acceptable salt thereof.

15. A compound of formula IG according to claim 1, which compound is:
1-(3,4-dihydro-2H-pyrido[3,2-b][1,4]oxazin-7-yl)-3,3-dimethyl-6-(2-methylpyrimidin-5-yl)indolin-2-one; or
3,3-dimethyl-1-(3-methylbenzo[d]isoxazol-5-yl)-6-(2-methylpyrimidin-5-yl)indolin-2-one, or a pharmaceutically acceptable salt thereof.

16. A compound of formula IH according to claim 1

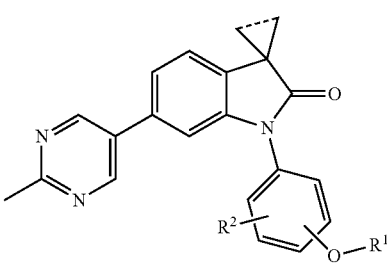

wherein
R¹ is hydrogen, lower alkyl, lower alkyl substituted by halogen or oxetanyl;
R² is hydrogen, lower alkyl lower alkoxy, halogen or cycloalkyl; and --- the dotted line is nothing or may be —$CH_2$—;
or a pharmaceutically acceptable salt thereof.

17. A compound of formula IH according to claim 16, which compound is:
   1-(3-methoxyphenyl)-3,3-dimethyl-6-(2-methylpyrimidin-5-yl)indolin-2-one, or a pharmaceutically acceptable salt thereof.

18. A combination of a compound of formula I according to claim 1 together with a known marketed antipsychotic, antidepressant, anxiolytic or mood stabilizer.

19. A combination according to claim 18, wherein the marketed antipsychotic drug is olanzapine, clozapine, risperidone, aripiprazole or ziprasidone.

20. A combination according to claim 18, wherein the marketed anti-depressive drug is citalopram, escitalopram, paroxetine, fluoxetine, sertraline, duloxetine, milnacipran, venlafaxine, or mirtazapine.

21. A combination according to claim 18, wherein the marketed anxiolytic drug is alprazolam, chlordiazepoxide, clonazepam, Estazolam, eszopiclone, zaleplon, zolpidem, pregabalin or gabapentin.

22. A combination according to claim 18, wherein the marketed mood stabilizer is
   Carbamazepine, Lamotrigine, Lithium, or Valproic Acid.

23. A process for preparation of a compound of formula I as described in claim 1, the process comprising:
   reacting a compound of formula

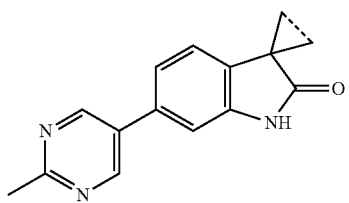

1 with a compound of formula

Y-A($R^2$)—O—$R^1$    2 to make a compound of formula

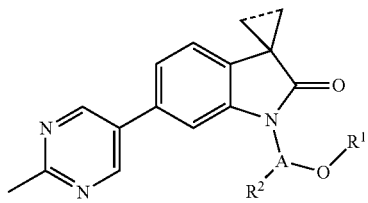

I wherein Y is Cl, Br or I and the other groups have the meaning as described in claim 1 and, if desired, converting the compound obtained into pharmaceutically acceptable salt.

24. A compound according to claim 1, whenever prepared by a process as claimed in claim 23.

25. A pharmaceutical composition comprising a compound in accordance with claim 1 and a therapeutically effective carrier.

26. A method for the treatment of CNS diseases related to positive (psychosis) and negative symptoms of schizophrenia, substance abuse, alcohol and drug addiction, obsessive-compulsive disorders, cognitive impairment, bipolar disorders, mood disorders, major depression, treatment resistant depression, anxiety disorders, Alzheimer's disease, autism, Parkinson's disease, chronic pain, borderline personality disorder, sleep disturbances, chronic fatigue syndrome, stiffness, asthma, Huntington's disease, ADHD, amyotrophic lateral sclerosis, arthritis, viral and fungal infections, ophthalmology and inflammatory retinal diseases and balance problems, epilepsy and neurodevelopmental disorders with co morbid epilepsy, which method comprises administering an effective amount of a compound as defined in claim 1.

* * * * *